United States Patent [19]

Manker

[11] Patent Number: 4,742,620
[45] Date of Patent: May 10, 1988

[54] BOWLING BALL WEIGHT LOCATING METHOD AND APPARATUS

[76] Inventor: Robin C. Manker, 160 E. Pennsylvania, S. Jacksonville, Ill. 62650

[21] Appl. No.: 24,777

[22] Filed: Mar. 11, 1987

[51] Int. Cl.$^4$ ............................................. G01B 3/14
[52] U.S. Cl. ........................................ 33/510; 33/21.2
[58] Field of Search .............. 33/21.1, 21.2, 509, 33/510

[56] References Cited

U.S. PATENT DOCUMENTS

| | | | |
|---|---|---|---|
| 1,175,612 | 3/1916 | Cresse | 33/21.2 |
| 3,161,041 | 12/1964 | Amburgey | 33/509 X |
| 3,875,668 | 4/1975 | Taylor | 33/509 X |
| 3,878,762 | 4/1975 | Goldsmith | 33/21.2 X |

*Primary Examiner*—Harry N. Haroian
*Attorney, Agent, or Firm*—Cohn, Powell & Hind

[57] ABSTRACT

A method and apparatus for determining: (1) the location of a weight block in a previously undrilled bowling ball; (2) locating thumb and finger grip holes and determining a depth for each hole on a previously undrilled bowling ball such that the bowling ball conforms to the bowler's balance specifications; (3) the same as in (2) above except that the location of the thumb and finger grip holes and depth of the holes are drilled in order that the bowling ball will be dynamically balanced; (4) locating a balance hole and determining the depth of the balance hole on a previously drilled bowling ball such that the bowling ball conforms to the bowler's balance specifications; and (5) the same as in (4) except that the location of the balance hole and the depth of the balance hole are drilled in order that the bowling ball will be dynamically balanced.

17 Claims, 5 Drawing Sheets

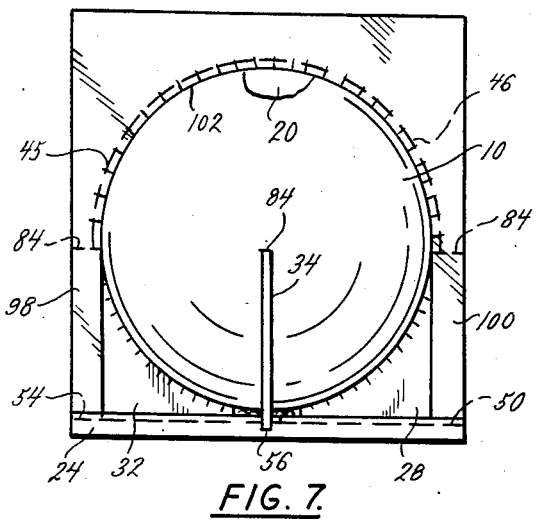
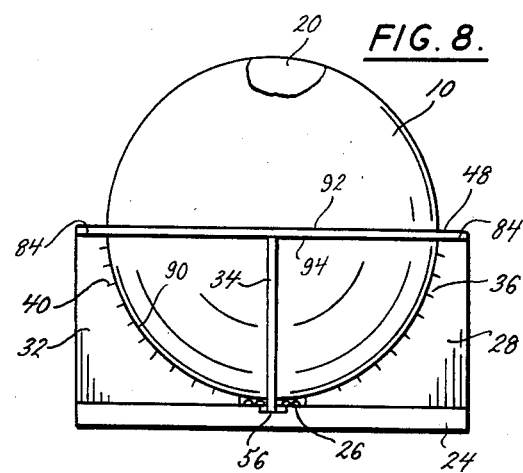
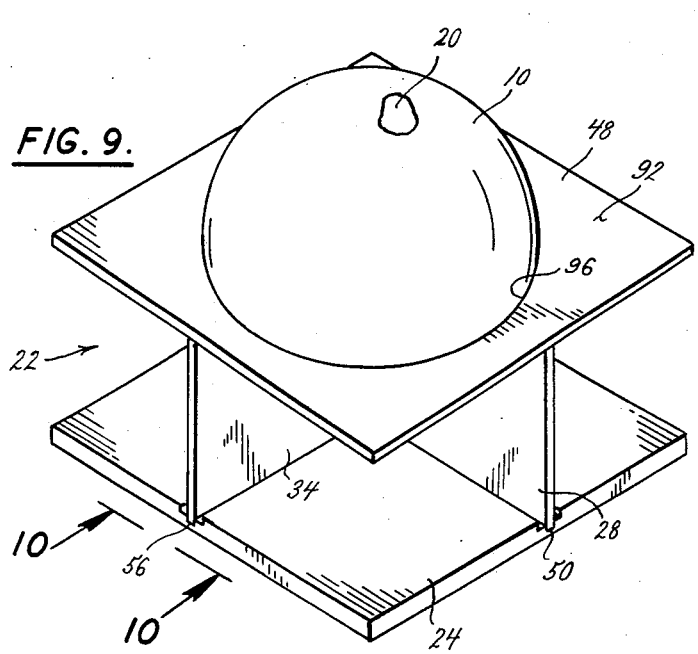
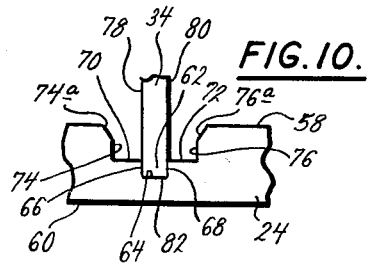
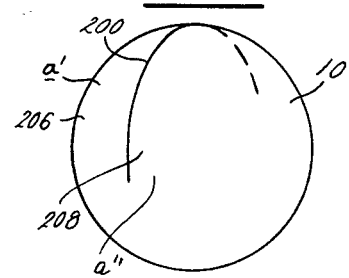
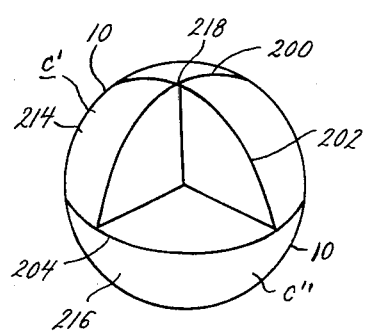
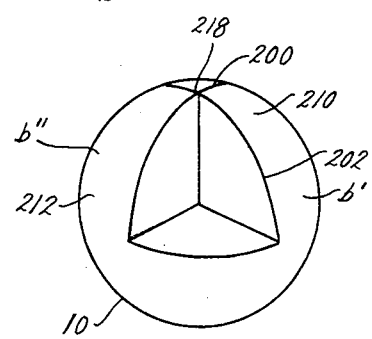

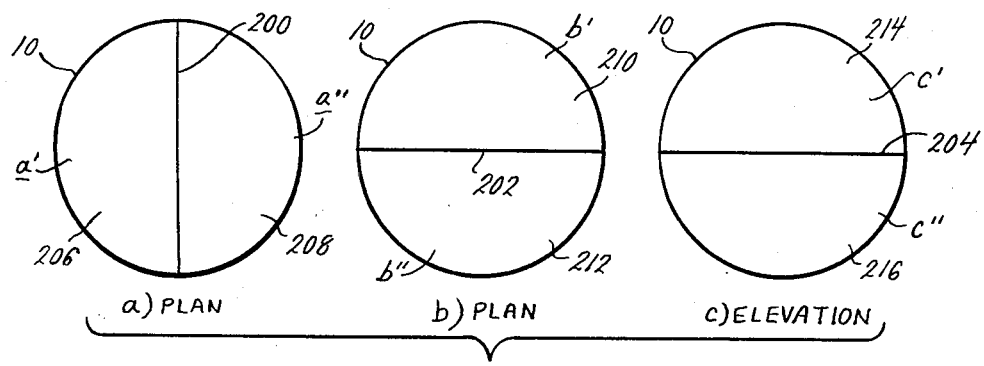
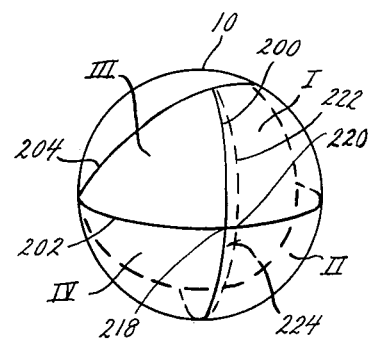
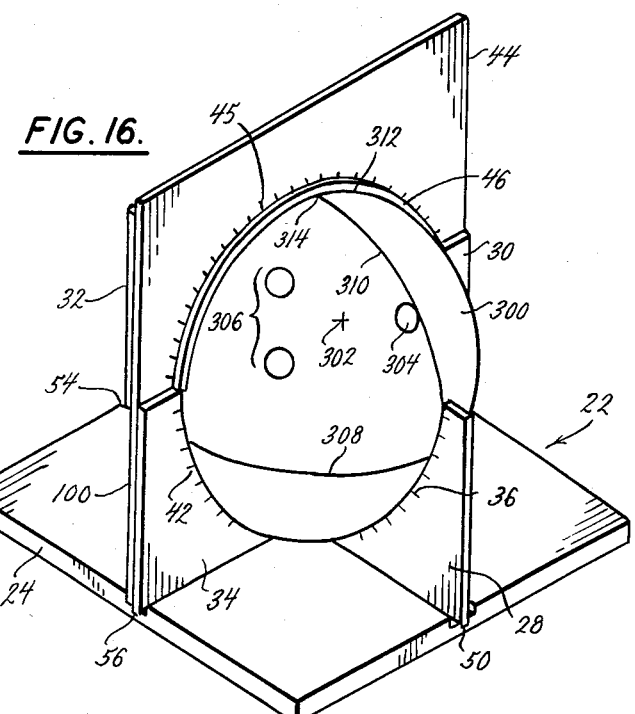
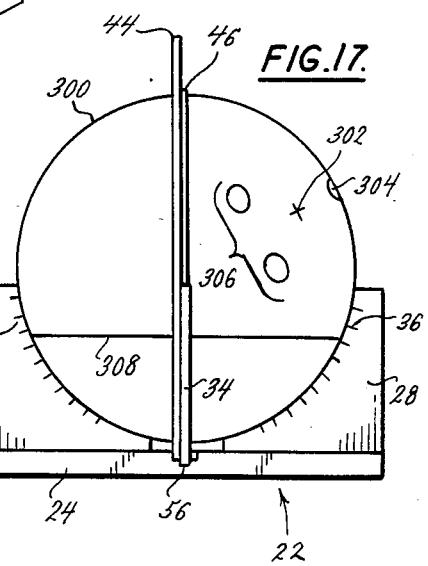
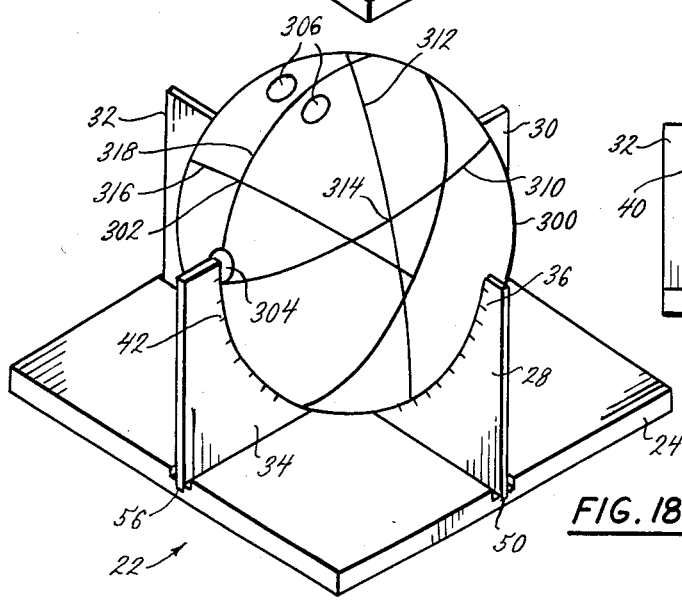

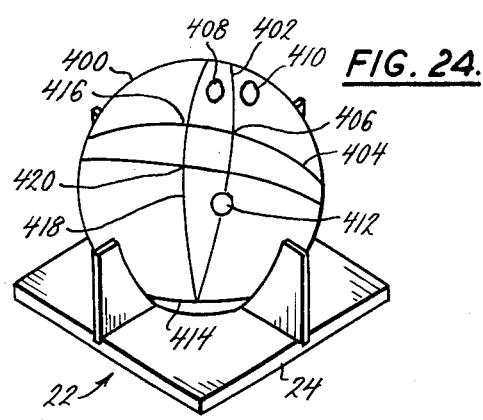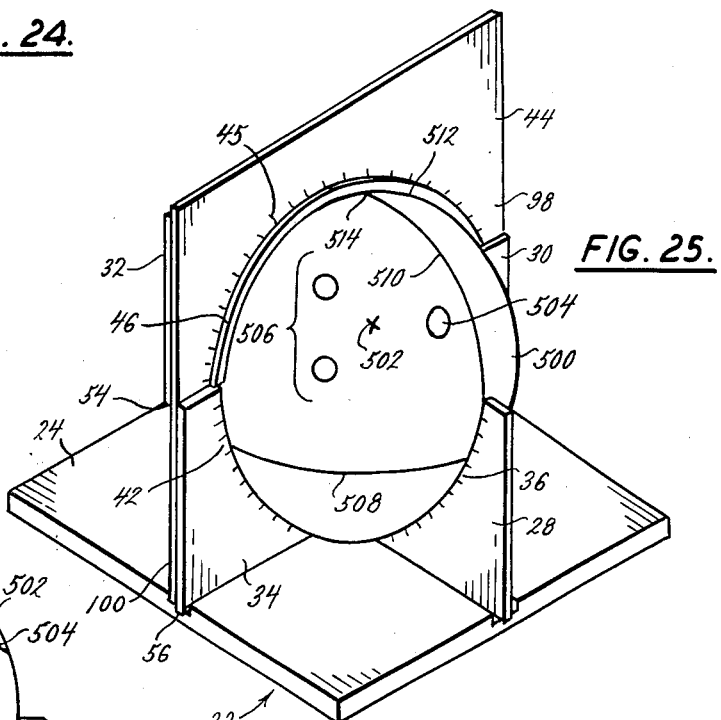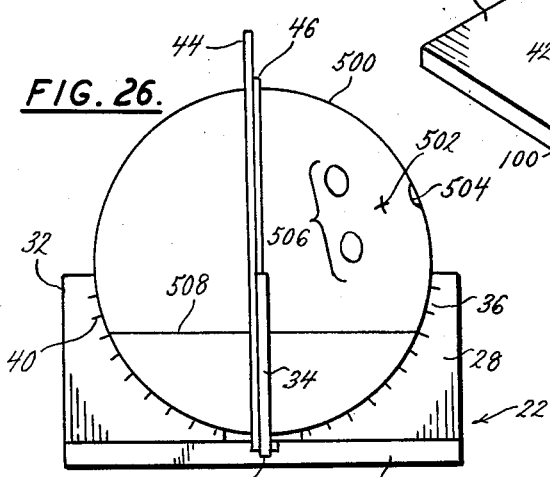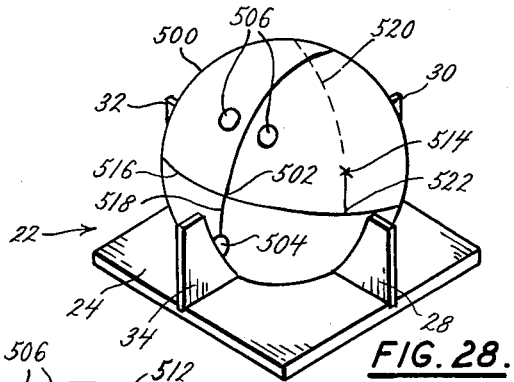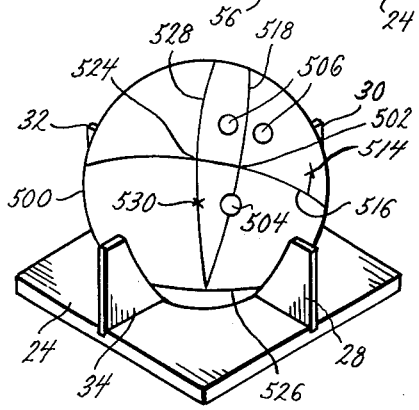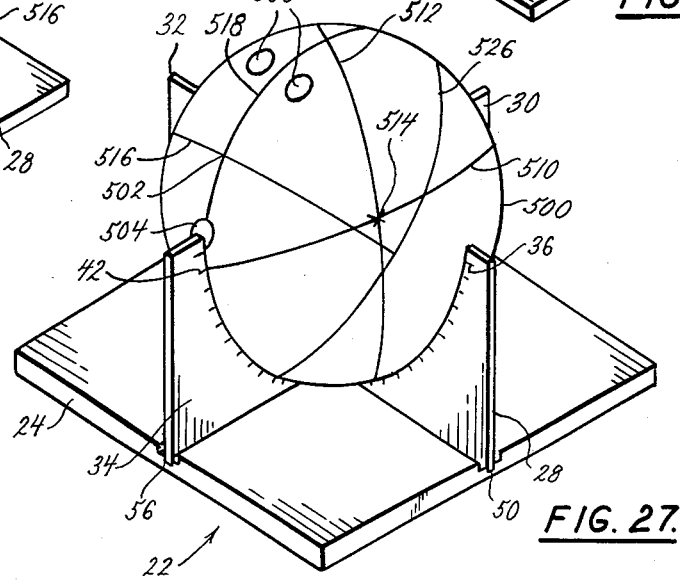

BOWLING BALL WEIGHT LOCATING METHOD AND APPARATUS

BACKGROUND OF THE INVENTION

This invention relates generally to a method for providing a desired weight imbalance in a bowling ball and apparatus for impelementing the method and more specifically to a method for accurately locating a reference point on an undrilled bowling ball, or locating finger and thumb holes for a bowler's grip or a balance hole on either an undrilled bowling bowl or a previously drilled bowling ball so as to provide a desired bowling ball imbalance or dynamic balance and apparatus for implementing the method.

All bowling balls are manufactured with a weight block or blocks (hereinafter referred to as a block since the number of blocks is immaterial for an understanding of the present invention) cast in the inner core material of the bowling ball. The purpose of the weight block is to counteract the change in the bowling ball's balance or relative imbalance resulting from drilling the bowling ball for finger and thumb grip holes.

Gripping holes for most bowling balls drilled today are over a manufacturer's label. Assuming that a bowling ball is labelled correctly, the bowling ball will have little, if any, side weight or finger weight but will probably have some top weight. This means that the bowling ball would come to rest with the gripping holes on the bottom if the ball were suspended in a medium such as mercury or on an air table and allowed to reach equilibrium. Wobble is a phenomenon that results from a bowling ball not being dynamically balanced (balanced as it rolls). A bowling ball that has zero side weight, zero finger weight, and zero top weight is said to be balanced statically that is, it weights the same in a dodo scale regardless of which way the bowling ball is positioned in the dodo scale. If a bowling ball has something other than zero for any of three weights, then the bowling ball will wobble as it rolls unless the three weights create a controlled imbalance. If a bowling ball has a controlled imbalance then it is said to be balanced dynamically. A bowling ball that is balanced statically will automatically be balanced dynamically but not the converse. The only exception is a dynamically balanced bowling ball with zero weight difference in three directions, top weight, side weight and finger weight. Instead of rolling smoothly, a dynamically unbalanced bowling ball pulsates as it rolls. This characteristic is usually caused by too much top weight. A relatively small weight can make a noticable difference on a relatively heavy ball.

The goal of operators of bowling ball drilling equipment is to drill a thumb and finger grip holes or a balance hole into a bowling ball relative to the location of the weight block within the bowling ball so that the removal of weight by drilling and the excess weight in the weight block will complement each other thus providing a bowling ball with a desired imbalance or dynamic balance. It should be understood that "desired imbalance" could include a statically balanced bowling ball, in which case the imbalance would be zero.

However, since bowler's handspans are different and fingers and thumbs are different sizes for different bowlers, it is extremely unlikely that material removed by drilling will be exactly offset by the extra mass of the weight block when relying on presently used methods, including trial and error, a driller's skill notwithstanding.

Presently, the actual location of a weight block in a bowling ball is never exactly known due to the lack of refinement in methods used by bowling ball manufacturers to mark a bowling ball at the factory. One method used by manufacturers has a laborer float a number of bowling balls in a mercury bath, spin the bowling balls and then return after the balls have supposedly stopped spinning. The laborer then marks the bowling balls with a "Manufacturer's Reference Point" or MRP.

In theory the MRP indicates the location of the weight block relative to an imaginary line from the geometric center of the bowling ball through the center of gravity of the bowling ball and through the bowling ball's outer surface. The MRP is supposed to indicate the location of an intersection of the imaginary line and the bowling ball surface, also called "center-of-palm". The MRP can be off by a considerable amount but the driller will never know before an incorrectly marked "MRP" bowling ball is drilled and perhaps ruined for a bowler.

Even if a bowling ball has a nearly correct MRP, other errors may be introduced by the driller of the bowling ball so as to offset the mass of the weight block. Drilling finger and thumb grip holes in a bowling ball requires the removal of material from the bowling ball. Drilling finger and thumb grip holes in a bowling ball becomes more of an art than a science, particularly if a bowler requests a particular weight imbalance, since the exact location of the weight block with its extra mass can not be exactly offset by known methods, for example, trial and error. Experience has shown that only through the use of unteachable skill and trial and error may a driller become skilled in the preparation of a bowling ball to meet a bowler's particular requirements and even the experienced driller will not be able to consistently meet the bowler's requirements for weight imbalance.

In addition to the above, the American Bowling Congress has established tolerances that pertain to the imbalance of a bowling ball in order to provide guidelines for acceptable imbalances of drilled bowling balls. Any bowling ball used in a competition sanctioned by the American Bowling Congress must conform to these specifications and nearly all bowling competitions are sanctioned by the American Bowling Congress.

The allowed tolerances have such a wide range that a bowling ball that conforms at one end of the range reacts on a bowling lane or alley much differently than a bowling ball that conforms to the other end of the specified range. The present invention enables each bowler to have a bowler requested desired imbalance (or balance) in his or her bowling ball. Alternatively, the present invention also enables a bowler to have optimum imbalance that may be determined by the present invention corresponding to dynamic balance. Dynamic balance may be determined from the location of a ball track on the surface of the bowling ball. Optimum imbalance refers to a bowling ball that is dynamically balanced.

The present method for providing a desired weight imbalance in a bowling ball and apparatus for performing the method solves these and other problems in a manner not disclosed in the known prior art.

SUMMARY OF THE INVENTION

The method for providing a desired weight imbalance in a bowling ball and the apparatus for implementing the method of the present invention provides a plurality of steps for determining an interrelationship between actual and desired weight imbalance in order to obtain a bowling ball with a desired weight imbalance as well as apparatus for implementing the steps. The present invention interrelates the steps of the method and the apparatus used to implement the steps of the method. By means of the present invention a bowler's new bowling ball may be drilled for finger and thumb grip holes or marked prior to drilling with an "Actual Reference Point" (ARP) or center-of-palm or a new balance hole may be drilled in a previously drilled bowling ball in order to correct errors from an inexact previous drilling or create a newly desired bowling ball weight imbalance. All of the above characteristics of the present invention allow the bowler to tailor his or her bowling ball to a desired weight imbalance or dynamic balance. The position of a ball track reflecting a particular dynamic balance and the side, finger, and top weight differences are interdependent to a certain extent. The ball track further depends upon a bowler's type of release and the weight differences required to achieve a desired weight imbalance.

If the center of gravity of a bowling ball coincides with the geometric center of the bowling ball, then the bowling ball is considered to be statically balanced. The relative static weights are identified as a side weight, a finger weight and a top weight. A balanced bowling ball indicates that the bowling ball is balanced statically. A perfectly balanced bowling ball indicates a zero side weight, a zero finger weight, and a zero top weight. If the center of gravity of a bowling ball lies on a line that contains the geometric center of the bowling ball and the center of the ball track, then the bowling ball would be dynamically balanced. Many bowlers do not want a bowling ball that is statically balanced but prefer a bowling ball that is dynamically balanced. For example, a typical bowling ball that is dynamically balanced for a right handed bowler might have 1.0 ounce side weight, 0.25 ounces finger weight, and 0.20 ounces top weight. It should be understood that the term balanced as used herein may include statically balanced bowling balls but generally refers to a dynamically balanced bowling ball.

A principal aspect of the present invention is to provide a method and apparatus for implementing the method to determine or provide the desired balanced bowling ball. For example, the method can be utilized for:

1. accurately locating the MRP of an undrilled bowling ball (primarily intended for use by bowling ball manufacturers);
2. locating the thumb and finger grip holes and determining the depth of the holes on a previously undrilled bowling ball such that the bowling ball conforms to the bowler's balance specifications or is dynamically balanced; and
3. locating a balance hole and determining the depth of the balance hole on a previously drilled bowling ball such that the bowling ball conforms to the bowler's balance specifications or is dynamically balanced.

In another aspect of the present invention a method is provided for accurately determining a desired balance or imbalance in a bowling ball without the need to use trial and error or guesswork in obtaining accurate results.

It is yet another aspect of the present invention to provide a method of determining a bowling ball's weight imbalance that is useable by operators of bowling ball drilling equipment and bowling ball manufacturers.

It is still another aspect of the present invention to provide an easy-to-use method of determining a bowling ball's weight imbalance that does not require the repeated weighing of a ball and the introduction of unnecessary errors.

In another aspect of the present invention a method is provided which incorporates the American Bowling Congress regulations regarding ranges of bowling ball imbalance. Additionally, the present method can be changed to reflect any revisions or amendments that might be promulgated by the American Bowling Congress with respect to the range of allowed weight imbalances.

In still another aspect of the present invention apparatus is provided utilizing new weighing equipment, apparatus and techniques. The utilization of some known techniques and apparatus, for example, a dodo scale, reduces the time required for those familiar with these techniques to learn the method and use of the present invention.

It is another aspect of the present invention that the method provided for determining a bowling ball's weight imbalance may be used by those relatively unskilled in the techniques of bowling ball drilling and even by a bowler having the necessary apparatus and ability to follow a few straightforward instructions in the use of the apparatus and method.

It is yet another aspect of the present invention that similar steps are used in various embodiments of the present invention. Thus, the use of the present invention is relatively easy to learn for a broad number of applications.

In another aspect of the present invention a method and apparatus for implementing the method of the present invention are provided capable of providing a balanced/imbalanced bowling ball based on either a bowler's specifications or location of the ball track as limited by the American Bowling Congress established balance ranges or any percentage thereof.

It is yet another aspect of the present invention that a bowler, particularly a seasoned veteran, may adjust the imbalance of a bowling ball to suit a particular need or for experimental purposes by utilizing the method of the present invention for determining a bowling ball's weight imbalance and the apparatus provided for implementing the method.

To accomplish the foregoing and other aspects of the invention there is provided a method and apparatus for determining a desired imbalance of a bowling ball. The steps comprising the method include placing a bowling ball in a ball cradle such that the outer surface of the ball is readily available for indicating a number of reference points to be determined by the method of the invention. It is understood that the bowling ball includes an internal weight block and has a given diameter and total weight. A pair of perpendicular arcs are marked on the surface of the bowling ball with the aid of the ball cradle, a plurality of wings, and an arc maker. The two arcs may intersect at a point identified as a Temporary Reference Point or TRP or previously determined MRP and a great circle is located on the surface of the ball such that the great circle is perpendicular to both arcs. A circular template intended to rest on the wings is used to make the great circle. The two arcs and the great circle define three (3) pairs of hemispheres, a first side of the bowling ball and a second side of the bowling ball, a finger side of the bowling ball and a thumb side of the bowling ball, and a top half of the bowling ball and a bottom half of the bowling ball.

After the arcs and great circle are marked on the bowling ball the bowling ball is removed from the cradle and weighed in a dodo scale to determine a relative side weight, a relative finger weight, and a relative top weight. The relative side weight corresponds to the difference between a first side weight of the bowling ball and a second side weight of the bowling ball as measured by the dodo scale. The relative finger weight corresponds to the difference between a finger side weight of the bowling ball and a thumb side weight of the bowling ball as measured by the dodo scale. The relative top weight corresponds to the difference between a top half weight of the bowling ball and a bottom half weight of the bowling ball as measured by the dodo scale.

A first coordinate and a second coordinate are determined relative to the TRP or MRP and the relative side weight, the relative finger weight and the relative top weight of the bowling ball. The bowling ball diameter is taken into account in determining the first coordinate and the second coordinate. Generally, the next step of the invention requires marking a second intersection point or ARP or actual reference point on the bowling ball surface. The ARP may be determined by the first coordinate and the second coordinate.

Further steps of the method of the present invention include determining a third coordinate and a fourth coordinate relative to the ARP or other previously identified reference point such that the third and fourth coordinates determine the location of either a second, new ARP or a balance hole on the surface of the bowling ball and the depths of the finger and thumb grip holes or a balance hole, respectively. The third and fourth coordinates are determined by a relationship between the relative side weight, the relative finger weight, the relative top weight, the bowling ball weight and diameter and either the bowler's desired imbalance for the bowling ball or the location of a ball track.

These and other aspects and features of the present invention will be better understood and appreciated from the following detailed description of particular preferred embodiments thereof, selected for the purpose of illustration and shown in the accompanying drawings.

BRIEF DESCRIPTION OF THE DRAWINGS

FIG. 7 is an elevation taken along line 7—7 in FIG. 4;

FIG. 8 is an elevation view of a bowling ball in a cradle and a circular template according to a preferred embodiment of the present invention;

FIG. 9 is a perspective view of the bowling ball and cradle with the circular template as illustrated in FIG. 8;

FIG. 10 is a detail of a typical intersection between a wing member and a base member of a preferred embodiment of the present invention;

FIG. 11 is a developmental perspective of a bowling ball illustrating the location of a first arc marked on the surface of the ball;

FIG. 12 is a developmental perspective of the bowling ball illustrating both the first and a second arc located on the surface of the bowling ball;

FIG. 13 is a developmental perspective of the bowling ball illustrated in FIGS. 11 and 12 illustrating both the first arc, second arc and a great circle located on the bowling ball surface;

FIG. 14 is a developmental perspective illustrating the relative locations of the finger and thumb weight, side weights and top and bottom weight of a bowling ball;

FIG. 15 is a developmental perspective illustrating the location of a plurality of arcs marked on the surface of a bowling ball and used to determine the ARP and illustrates a horizontal and a vertical coordinate as used in the following description of the preferred embodiments of the present invention;

FIG. 16 is a perspective similar to FIG. 3 illustrating the method by which weight differences required to achieve dynamic balance may be determined on a previously drilled bowling ball;

FIG. 17 is an elevation of the bowling ball and cradle of FIG. 16;

FIG. 18 is a developmental perspective illustrating one relationship between a center-of-palm and axis of roll;

FIG. 24 is a developmental perspective of a bowling ball illustrating the development of the location of a balance hole relative to a center-of-palm for a previously drilled bowling ball;

FIG. 25 is a perspective illustrating the method by which the axis of roll of a previously drilled bowling ball may be developed;

FIG. 26 is an elevation of the bowling ball and cradle of FIG. 25;

FIG. 27 is a developmental perspective illustrating a relationship between a center-of-palm and axis of roll for a previously drilled bowling ball;

FIG. 28 is a simplified version of the developmental perspective illustrated in FIG. 27; and FIG. 29 is a developmental perspective illustrating the relationship between the center-of-palm, axis of roll and new balance hole for a previously drilled bowling ball.

DESCRIPTION OF THE PREFERRED EMBODIMENT

In order to appreciate the method of the present invention it will be advantageous to first be familiar with apparatus used to practice the method consisting of apparatus of a preferred embodiment generally illustrated in FIGS. 3–10. However, it will be important to first generally describe a bowling ball's internal and external structure.

Figure 1:
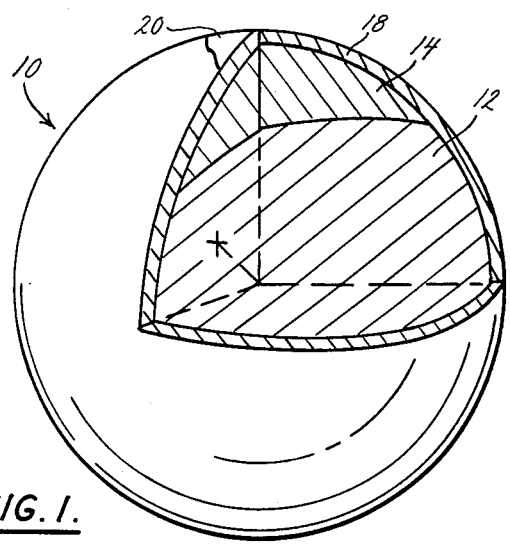
FIG. 1 is a perspective view of a bowling ball with approximately one-eighth of a sphere removed.
Figure 2:
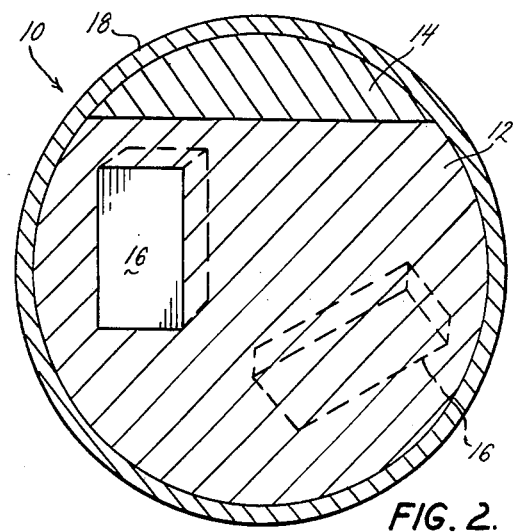
FIG. 2 is a cross-section of a bowling ball illustrating alternative weight block locations.

A bowling ball 10, as generally illustrated in FIGS. 1 and 2, includes three weight contributing elements. They are an inner core 12, a weight block 14 (or one of several alternatives located as indicated by reference character 16) and an outer shell 18. The dissimilar densities of the weight contributing elements of the bowling ball form a complicated dynamic system when the bowling ball is sent down a bowling alley by a bowler. A typical bowling ball is a sphere approximately nine (9) inches in diameter weighing anywhere from eight (8) to sixteen (16) pounds into which at least one mass of greater density (the weight block) is cast. The interrelationship of the different density portions is complicated by the fact that material of at least two (2) different densities may be removed for either a plurality of grip holes or a balance hole or both.

A manufacturer's label (or MRP) 20 is usually placed on each bowling ball before shipping from the manufacturer in order to indicate to a bowling ball driller the approximate location of the weight block 14 within the inner core 12 of bowling ball 10. The purpose of the MRP is to locate the portion of the bowling ball to be drilled so as to counteract the change in the bowling ball's balance or relative imbalance resulting from drilling the bowling ball. The goal of operators of bowling ball drilling equipment is to drill a thumb and a pair of finger grip holes or a balance hole into the bowling ball relative to the location of the weight block so that the removal of weight by drilling and the excess weight in the weight block will complement each other thus providing either a bowling ball with a desired imbalance or a dynamically balanced bowling ball with a desired axis of roll. It should be understood that "desired imbalance" could include a statically balanced bowling ball. If the MRP is inaccurately located on a bowling ball then a successful drilling operation becomes very difficult if not impossible.

Furthermore, since bowler's hand spans are different and fingers and thumbs are different sizes for different bowlers, it is extremely unlikely that a static balance change due to drilling will be exactly cancelled by the weight block even if the MRP is accurately located because of the complex interrelationship between a bowling ball's weight imbalance and the location of a bowling ball's track.

In order to appreciate the steps of the present invention now that the structure of the typical bowling ball has been described, it will be advantageous to further discuss a preferred embodiment of the apparatus used to perform the steps of the method.

Referring now by characters of reference to drawings FIGS. 3–10 it will be understood that a preferred embodiment of the apparatus used to perform the steps of the method of the present invention generally includes means for supporting a bowling ball. In a preferred embodiment the means includes a ball cradle 22 and a plurality of component members. The ball cradle 22 includes a base 24 with rotatable means for supporting the bowling ball such as an integral ball bearing support 26 and a first and second means for defining perpendicular planes, such as a plurality of wing members, a first wing 28, second wing 30, third wing 32 and fourth wing 34. The first and third wings define a first plane and the second and fourth wings define a second plane perpendicular to the first plane.

Some of the steps of the method of the present invention require a particular alignment of the bowling ball in the cradle 22. For this reason each wing preferably but not necessarily includes a reference scale. A first wing reference scale 36, second wing reference scale 38, third wing reference scale 40 and fourth wing reference scale 42 are illustrated such that there is a correspondence between the reference scales and an imaginary plane parallel to base 24 intersects each wing 28, 30, 32 and 34 at corresponding points on reference scales 36, 38, 40 and 42.

Other components of a preferred embodiment of the apparatus include means for locating a semicircular arc on the bowling ball surface. In a preferred embodiment the locating means includes a semicircular template 44, also referred to as an arc maker including shoulder 46 and a circular template 48 as a means for locating a great circle on the surface of the bowling ball. These components will be described in further detail below.

In order to perform the steps of the method of the present invention it is necessary to mark a plurality of arcs on the surface of outer shell 18 such that certain of the arcs intersect at right angles. The wings 28, 30, 32 and 34 cooperate with semicircular template 44 to provide guides for marking the arcs on the surface of the bowling ball. Since adjacent wings define perpendicular planes it is a relatively easy matter to locate and mark pairs of perpendicular arcs when the components of the ball cradle 22 are used as set forth more fully below.

The wings 28, 30, 32 and 34 are operatively associated with the support means. In a preferred embodiment the wings are supported by corresponding wing receiving channels 50, 52, 54 and 56. With reference now to FIG. 10, typically, each channel is formed in an upper face 58 of base 24. The ball cradle 22 is generally supported on a work surface with the lower face 60 of base 24 resting upon the work surface. In one preferred embodiment the wing receiving channels are identical and a typical one will now be described in greater detail in which typical characters of reference will be referred to and used for the typical structure and respective structure of each channel 50, 52 and 54, also.

Each channel includes a central axial groove 62 for receiving the corresponding or respective wing. Each groove has a bottom surface 64 on which the respective wing rests and first and second opposing sidewalls 66 and 68 which support the wing generally perpendicular to base 24 of ball cradle 22. Located above, on either side and generally parallel to central groove 62 are upwardly directed shoulders 70 and 72 and opposing sidewalls 74 and 76. A corner of each sidewall 74, 76 has a chamfer 74a, 76a, respectively, providing, for example, easy insertion of template 44 into a desired position.

Figure 6:
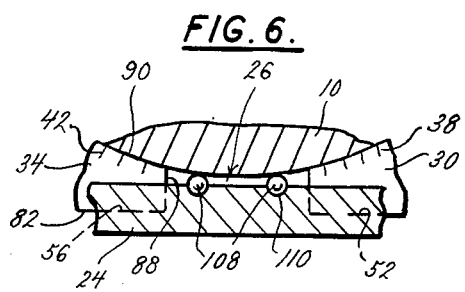
FIG. 6 is a partial section taken along line 6—6 in FIG. 3.

Each wing in a preferred embodiment has opposing vertical faces 78, 80, a bottom edge 82 and a top edge 84. Bottom edge 82 is the edge that rests on respective bottom surface 64 of central groove 62. Each wing includes two vertical edges, a long vertical edge 86 located towards the outside edge of base 24 and a short vertical edge 88 located towards the center and the general location of ball bearing support 26. Connecting edges 84 and 88 of each wing is a curved edge 90, as shown in FIG. 6, which is generally parallel to the surface of outer shell 18 of bowling ball 10. In a preferred embodiment, clearance between curved edge 90 and shell 18 of the bowling ball is kept to a minimum.

In order to perform the steps of the method of the present invention it is sometimes necessary to mark a great circle or circles on the surface of outer shell 18. To this purpose there is provided means for locating a great circle on the surface of the bowling ball. The great circle locating means may be supported by the wings. In a preferred embodiment, the great circle locating means includes a template 48 which in one preferred embodiment includes an upper face 92, a bottom face 94 and a circular inner template edge 96 as illustrated in FIG. 9. Top edge 84 of each wing supports circular template 48 in such a manner relative to the bowling ball 10 in ball cradle 22 that using the upper face 92 as a guide to mark the surface of the bowling ball in the ball cradle provides a guide with which to mark a great circle on the bowling ball.

Figure 5:
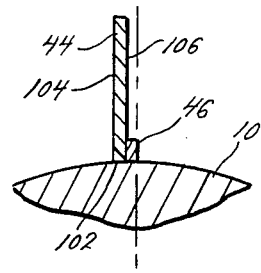
FIG. 5 is a partial section taken along line 5—5 in FIG. 3.

Semicircular template 44, as previously described, is supported on either first shoulder 70 or second shoulder 72 of respective wing receiving channels. Template 44 has first and second depending legs 98 and 100 and a curved edge 102. Curved edge 102 is generally parallel to the surface of outer shell 18 of bowling ball 10 and provides minimum practical clearance with outer shell 18. Each depending leg is supported generally parallel to the associated opposing wing pairs, either 28 and 32 or 30 and 34, by the wing on one side and either sidewall 74 or 76 on the other side. A purpose of the wings and semicircular template 44 is to provide an edge that can be used as a guide for marking an arc on bowling ball 10 that corresponds to the center line of the wing as shown in FIG. 5. For this purpose shoulder 46 is attached to one face of the semicircular template 44. In the illustrated embodiment, of the two faces 104 and 106 of semicircular template 44, shoulder 46 is attached to face 106.

The bowling ball 10 is supported on ball cradle 22 by a plurality of ball bearings 108 in a circular groove or ball race 110. The use of ball bearings or any other equivalent support means allows the bowling ball 10 to be freely rotated in order to mark the necessary reference marks on the bowling ball in order to perform the steps of the method of the preferred embodiment as will now be described in greater detail.

The steps of the method of the present invention, as generally illustrated in FIGS. 11–29, will be described for five (5) preferred embodiments chosen for purposes of illustration and description of the present invention. (In one embodiment in particular, the method provides steps to locate an accurate MRP on a previously undrilled bowling ball. It is believed that this embodiment will be particularly useful to manufacturers of bowling balls and could take the place of presently used, inefficient and inaccurate methods.)

The five (5) preferred embodiments set forth herein are:
1. locating an accurate MRP of an undrilled bowling ball;
2. locating thumb and finger grip holes and determining a depth for each hole on a previously undrilled bowling ball such that the bowling ball conforms to the bowler's balance specifications;
3. the same as in 2. above except that the location of the thumb and finger grip holes and depth of the holes are drilled in order that the bowling ball will be dynamically balanced;
4. locating a balance hole and determining the depth of the balance hole on a previously drilled bowling ball such that the bowling ball conforms to the bowler's balance specifications; and
5. the same as in 4. except that the location of the balance hole and the depth of the balance hole are drilled in order that the bowling ball will be dynamically balanced.

Before providing further description of the steps of the method of the present invention it will be advantageous to the understanding of the steps to briefly describe one additional piece of apparatus. A means for determining a plurality of relationships between a plurality of vectors so as to determine the coordinates at which to drill grip holes or balance holes is provided.

Figure 22:
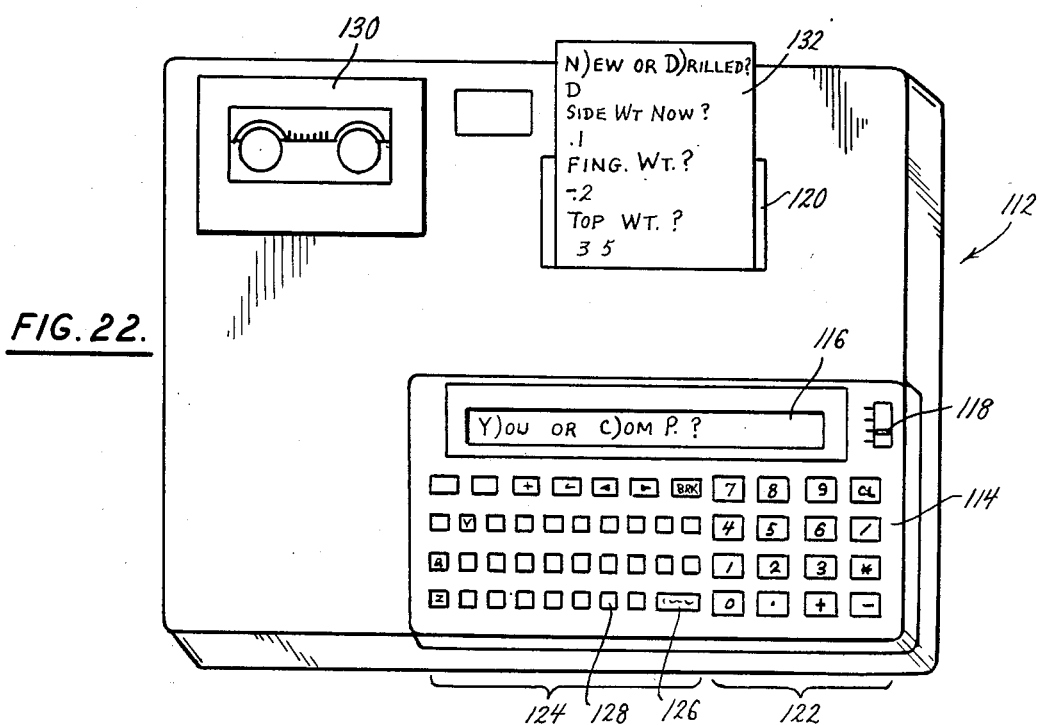
FIG. 22 is a perspective view of a portable computer suitable for use with the present invention.

Referring now by characters of reference to FIG. 22, in a preferred embodiment a pocket computer 112 is provided, such as a SHARP brand pocket computer Model PC-1250A. Pocket computer 112 includes keyboard 114 and liquid crystal display (LCD) screen 116. The pocket computer is controlled for both programming and running a program by means of multi-position switch 118. An optional, auxilliary printer 120 may also be included in a package containing the pocket computer.

Keyboard 114 includes a numerical keypad 122 and an alphabetical keypad 124. Keypad 124 includes a number of control and function keys. An enter key 126 and a space key 128 are used extensively when performing the steps of the present invention requiring the use of pocket computer 112. The illustrated embodiment of pocket computer 112 includes at least one other option, a tape drive 130 that could be used to store a program or data base. The use of an optional printer provides for a copy 132 of the results of each bowling ball that is processed according to the present invention.

Referring now by characters of reference to drawings FIGS. 11–14 it will be understood that a preferred embodiment of the method of the present invention generally includes the steps of marking a pair of perpendicular arcs 200 and 202 and a great circle 204 on outer shell 18 of bowling ball 10. The great circle 204 is located on the outer shell 18 of bowling ball 10 so as to be perpendicular to both arcs 200 and 202. As illustrated in FIGS. 11 and 14a, arc 200 divides the bowling ball into two hemispheres a' and a". These hemispheres will be referred to as first side 206 and second side 208. As illustrated in FIGS. 12 and 14b, arc 202 divides the bowling ball into two hemispheres b' and b" which will be referred to as finger side 210 and thumb side 212. Finally, as illustrated in FIGS. 13 and 14c, a great circle 204 divides the bowling ball into two hemispheres c' and c". These hemispheres will be referred to as top 214 and bottom 216.

As previously discussed, bowling ball manufacturers use a manufacturer's reference point or MRP or center of palm that they determine as a means for identifying the location of the weight block within the bowling ball in order that the bowling ball driller can determine where to place the finger and thumb grip holes and in some instances a balance hole. However, an accurate method of obtaining the location of the MRP or manufacturer's reference point is needed in order to increase the driller's accuracy. The method of the present invention may be used either by a manufacturer to initially locate a manufacturer's reference point or MRP on each bowling ball or it can be used by the driller in order to check the validity and accuracy of an existing MRP or determine the correct location of the MRP or center of palm on a bowling ball that was originally mismarked by a manufacturer.

Figure 4:
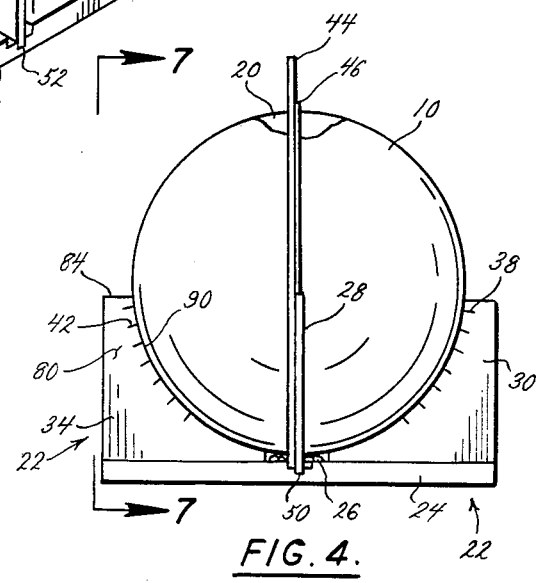
FIG. 4 is an elevation of a bowling ball in the cradle as shown in FIG. 3.

The driller or the manufacturer begins by placing a bowling ball with a mark placed on it by the manufacturer or without any marks on it, respectively, in the ball cradle. It will be understood that initially the driller or manufacturer knows that the bowling ball has an internal weight, an outer surface and a known diameter. Once the ball is positioned in the ball cradle as generally illustrated in FIG. 4 the semicircular template 44 may be located, for example, within first and third channels 50, 54. The driller continues by marking a first arc 200 on the surface of the bowling ball in cooperation with the ball cradle and the semicircular template. The first arc as illustrated in FIG. 11 defines the first side of the bowling ball a' and the second side of the bowling ball a''. These correspond to the first side 206 and second side 208 as defined by first arc 200.

The driller then takes the semicircular template 44 and places it in second channel 52 and fourth channel 56. The driller, using shoulder 46 as in the previous operation, continues by marking a second arc 202 on the surface of the bowling ball in cooperation with the cradle and the semicircular template. The second arc 202 and first arc 200 are perpendicular. It will be understood that shoulder 46 is used when marking arcs with semicircular template 44. The second arc defines a finger side of the bowling ball 210 or b' and a thumb side of the bowling ball 212 or b''. The intersection of the first arc and second arc define a first intersection point or reference point 218 or Temporary Reference Point (TRP).

It will be understood that first intersection point 218 may coincide with a manufacturer marked MRP or, alternatively, may represent a temporary reference point or TRP, used by the driller, for example, for convenience or expediency. A TRP may be useful in determining an ARP or center-of-palm but the location of an ARP is generally independent of any particular TRP initially selected by the driller.

FIGS. 11-13 illustrate the development of the intersecting arcs and a great circle 204 outside of the environment of the ball cradle. In order to illustrate the perpendicular relationships between the first and second arcs and the great circle an eighth section of the sphere of the bowling ball has been removed for the purpose of illustration only in FIGS. 12 and 13.

After marking the first arc and second arc on the surface of the bowling ball the driller removes the semicircular arc from the ball cradle 22 and places circular template 48 in position. It should be understood that it has not yet been necessary to move the bowling ball from its original position in the ball cradle. The driller continues by marking a great circle 204 on the surface of the bowling ball in cooperation with the cradle 22. The great circle is perpendicular to both the first and second arcs. The great circle defines a top half of the bowling ball 214 or c' and a bottom half of the bowling ball 216 or c''. FIG. 14 generally illustrates the division of the bowling ball into three pairs of hemispheres.

After the above-described reference lines have been marked on the surface of the bowling ball the driller takes the bowling ball to a dodo scale, a scale commonly used by bowling ball drillers, to measure relative weights between pairs of hemispheres of the bowling ball. The driller takes the bowling ball, places it in the dodo scale and by weighing it in a well-known fashion determines a relative side weight corresponding to a difference between a first side weight of the bowling ball and a second side weight of the bowling ball. The first side weight of the bowling ball corresponds to the first side 206 of the bowling ball and the second side weight of the bowling ball corresponds to the second side 208 of the bowling ball. The driller rotates the bowling ball in the dodo scale in a well-known fashion and continues by weighing the bowling ball to determine a relative finger weight. The relative finger weight corresponds to a difference between a finger side weight of the bowling ball and a thumb side weight of the bowling ball. The finger side weight and thumb side weight correspond to the finger side 210 of the bowling ball and thumb side 212 of the bowling ball, respectively.

Rotating the bowling ball again in the dodo scale in a known fashion, the driller continues by weighing the bowling ball to determine a relative top weight. The relative top weight corresponds to a difference between a top half weight of the bowling ball and a bottom half weight of the bowling ball. The top half weight corresponds to the top 214 and the bottom half weight correspond to the bottom 216 of the bowling ball as defined by great circle 204.

Once the relative weights are determined by weighing the bowling ball in the dodo scale, the driller continues by determining a first coordinate and a second coordinate relative to the first intersection point and a desired relationship between the relative side weight, the relative finger weight, the relative top weight, the ball weight and the ball diameter.

EXAMPLE I

As a first example, locating an accurate MRP, Example I, and the subsequent steps of the method, specific values will be used and operation of the pocket computer will be further described. It should be understood that the pocket computer includes a software package or operating system that will be further described in detail. For the purposes of Example I and all of the following examples, operation of the pocket computer will now be described.

It should be understood that the pocket computer is used to facilitate the determination of various coordinates such as a first coordinate and a second coordinate in the present example. In order to further understand the operation of the pocket computer referring again to FIG. 22, it will be seen that the pocket computer 112 further includes the numerical keypad 122 and the alphabetical keypad 124. Two special function keys, the ENTER key 126 and SPACE key 128 are located in the alphabetical keypad portion 124 of pocket computer 112. The following TABLE I of EXAMPLE I will illustrate the series of inputs and outputs in the form of, for example, messages on the LCD 116 or auxilliary printer 120. Prior to using the pocket computer an operating system is loaded into the pocket computer's memory either manually through the keyboard, through the tape drive 130, or through any other option provided on the pocket computer used.

Use of the pocket computer to determine the first and second coordinates starts by the user or bowling ball driller placing the switch 118 in the RUN position. After a short pause, a message, as illustrated in LINE 1 of TABLE I, appears on LCD 116. "COMPUTER:" and "DRILLER:" have been included in TABLE I and all the following examples to identify the source of the particular message on the LCD. When "COMPUTER:" or "C:" appears on a line next to a message this indicates a message generated by the operating system on the pocket computer. When "DRILLER:" or "D:" appears on a line this indicates input provided by the user such as the bowling ball driller. The user uses both the letter keys and the number keys to input the necessary data. The SPACE key is used to provide the necessary spaces within the input data. The ENTER key indicates to the computer operating system that the particular data entry step is complete and that the computer operating system should continue to the next operation. Striking the ENTER key is represented in the following tables as "[E]" and striking the SPACE key is represented as "[SPC]" for purposes of simplification.

For the purposes of EXAMPLE I it should be presumed that the following data have been obtained after locating arcs 200,202 and great circle 204 and weighing the bowling ball in the dodo scale.

Relative side weight equals 0.1 oz.
Relative finger weight equals −0.2 oz.
Relative top weight equals 3.5 oz.

It should be understood that the foregoing weights were presumably measured by the dodo scale relative to the first arc, second arc and great circle marked on the surface of the bowling ball as previously described. The bowling ball diameter is generally included as a defined value in the operating system and need not be input by the operator.

TABLE I

| Line 0 | DRILLER: RUN [E] |
|---|---|
| Line 1 | COMPUTER: N)EW OR D)RILLED? |
| Line 2 | DRILLER: D [E] |
| Line 3 | C: SIDE WT. NOW? |
| Line 4 | D: .1 [E] |
| Line 5 | C: FING. WT. ? |
| Line 6 | D: −.2 [E] |
| Line 7 | C: TOP WT. ? |
| Line 8 | D: 3.5 [E] |
| Line 9 | C: Y)OU OR C)OMP.? |
| Line 10 | D: Y [E] |
| Line 11 | C: DES. SIDE WT.? |
| Line 12 | D: 0 [E] |
| Line 13 | C: DES. FING. WT.? |
| Line 14 | D: 0 [E] |
| Line 15 | C: DES. TOP WT.? |
| Line 16 | D: 0 [E] |
| Line 17 | C: GO HORIZ. |
| Line 18 | D: [E] |
| Line 19 | C: 1./8. IN. |
| Line 20 | D: [E] |
| Line 21 | C: GO VERT. |
| Line 22 | D: [E] |
| Line 23 | C: −1./4. IN. |
| Line 24 | D: [E] |
| Line 25 | C: REMOVE 3.51 OUNCES |
| LINE 26 | D: [E] |
| Line 27 | C: — |

The first message appearing on the LCD is represented in Line 1 of TABLE I. In order to accurately determine the MRP of a newly manufactured bowling ball the operator or driller presses the "D" key on the alphabetical key pad 124 and then the ENTER key 126. Pressing the ENTER key signals to the operating system that the next operation should be commenced and this operation is represented in Line 3 of TABLE I. At this point the operating system requires the input of the relative side weight which is accomplished at Line 4.

Lines 3-8 illustrate input corresponding to the relative weights measured by the dodo scale. At Line 9 the operating system requests a decision whether the desired imbalance or desired relative side weight, desired relative finger weight and desired relative top weight will be chosen by the driller or by a subroutine included in the operating system. For the purposes of EXAMPLE I the driller indicates at Line 10 that the desired side weight, finger weight and top weight will be chosen by the user.

There may be a slight pause between Line 16 and Line 17 during which time the necessary determinations are being made in accordance with the operating system. When the determination of the operating system is complete the message of Line 17 appears. For the purposes of this embodiment it is necessary at the end of Line 17 for the driller to press the ENTER button as indicated in Line 18 in order for the operating system to continue to provide the value of the first coordinate in order to determine a second intersection point 220 as shown in FIG. 15. The second coordinate will be determined from Lines 21-24 in order to locate MRP 224. Line 25 displays the weight difference that may be attributed to the weight block 14 in the bowling ball. At Line 26 the driller strikes the ENTER key once again and Line 27 shows the message on the LCD indicating that the operating system has reached the end and can be restarted either by turning the pocket computer off and then on again to the RUN position or again typing "RUN" on the alphabetical key pad and hitting the ENTER key without turning the pocket computer off.

At this point it has been determined that the weight block is located beneath MRP 224. The intersection point 224 corresponds to the actual MRP or center-of-palm for the bowling ball as determined by the present invention.

Reference is made again to FIG. 15 in order to illustrate a coordinate system adopted for purposes of the present invention. It will be understood that the dimension given at Line 19 will be either positive, negative or zero. It should be further understood that the dimension given in Line 23 also will be either positive, negative or zero. For example, if the third intersection point 224 happens to coincide with a TRP originally chosen for the bowling ball by the driller then both Lines 19 and 23 will result in dimensions of zero inches. TABLE IA indicates a quadrant on the surface of the bowling ball in which the third intersection point 224 will be located as a function of the combination of the positive and negative values of the dimensions provided in Lines 19 and 23. (The term "BTWN" indicates that the intersection point is located on either arc 200 or arc 202 "between" the identified quadrants.)

TABLE IA

| Line 19 Value | + | + | − | − | 0 | 0 | + | − |
|---|---|---|---|---|---|---|---|---|
| Line 23 Value | + | − | + | − | + | − | 0 | 0 |
| Quadrant | I | II | III | IV | ARC 200 BTWN I and | ARC 200 BTWN II and | ARC 202 BTWN I and | ARC 202 BTWN III and |

TABLE IA-continued

| III | IV | II | IV |
|---|---|---|---|

The actual MRP 224 is located on a third arc 222 marked on outer shell 18 of the bowling ball 10. Second intersection point 220 is located in either the "positive" or "negative" direction along second perpendicular arc 202 corresponding to the value of the first coordinate (Line 19). In a preferred embodiment the units of the first and second coordinates are inches. It is advantageous to use either a flexible ruler to measure the first coordinate and the second coordinate on the outer shell 18 of the bowling ball 10 or rotate (or place) the bowling ball in ball cradle 22 and use a reference scale 45 on template 44. Preferably the reference scale 45 is divided into units corresponding to the units of the first and second coordinates displayed at Lines 19 and 23 of TABLE I, respectively.

In Example I the first coordinate is determined to be ⅛ inch measured in a positive direction from first intersection point 218. The driller of manufacturer measures ⅛ inch to the right (as illustrated in FIG. 15) and marks second intersection point 220. Then, preferably using the cradle 22, a pair of wings and template 44, third arc 222 is marked on outer shell 18 of bowling ball 10. It will be noted that arc 222 is perpendicular to second arc 202 as it passes through arc 202 at intersection point 220.

In Example I the second coordinate is determined to be ¼ inch measured in a negative direction. Thus, the third intersection point or MRP 224 is located by measuring ¼ inch along arc 222 in the previously defined negative direction as illustrated in FIG. 15. The driller or manufacturer has now located an accurate MRP or ARP, or center-of-palm, that is, the intersection point between the surface of bowling ball 10 and an imaginary line that passes through the bowling ball's geometric center and center of gravity. The center of gravity lies between the geometric center of the bowling ball and point 224.

EXAMPLE II

In another preferred embodiment the method of the present invention may be used to locate thumb and finger grip holes and determine the depth for each hole on a previously undrilled bowling ball such that the bowling ball conforms to the bowler's balance specifications or desired balance.

Manufacturers of bowling balls place small marks on the bowling balls generally in order to assist the driller. This mark has already been referred to as the manufactuer's reference point or MRP. The relative side weight, relative finger weight and relative top weight of a bowling ball are preferably measured with respect to this reference point. However, as already discussed, an MRP located by a manufacturer may differ from the actual reference point or ARP making it practically impossible to place the finger and thumb grip holes or a balance hole in a desired location. However, it should be understood that the present invention allows any point on the outer shell of the ball to be used as a temporary reference point of TRP. The MRP is used in EXAMPLE II for convenience and expediency.

EXAMPLE II illustrates the use of the present invention to accurately determine the location of an ARP or center-of-palm of a new, previously undrilled bowling ball in order to then drill finger and thumb grip holes in the bowling ball and provide a drilled bowling ball having a desired weight imbalance. The ARP is to be determined in accordance with a bowler's desired weight imbalance. After locating the ARP it will be understood that the driller may accurately drill the necessary grip holes for finger and thumb grips using standard bowling ball drilling techniques but accurately only because the present invention was used.

Figure 3:
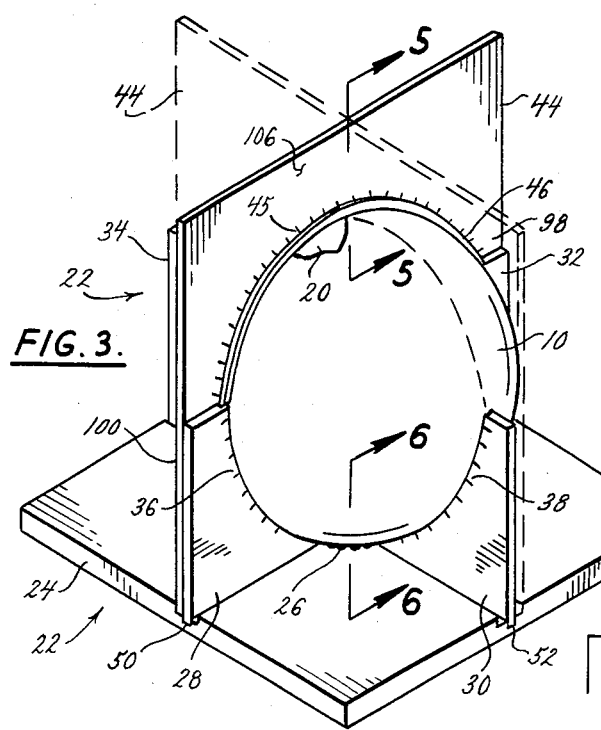
FIG. 3 is a perspective of a bowling ball and a cradle including a plurality of wings and an arc maker of a preferred embodiment of the present invention.
Figures 20, 21, 23:
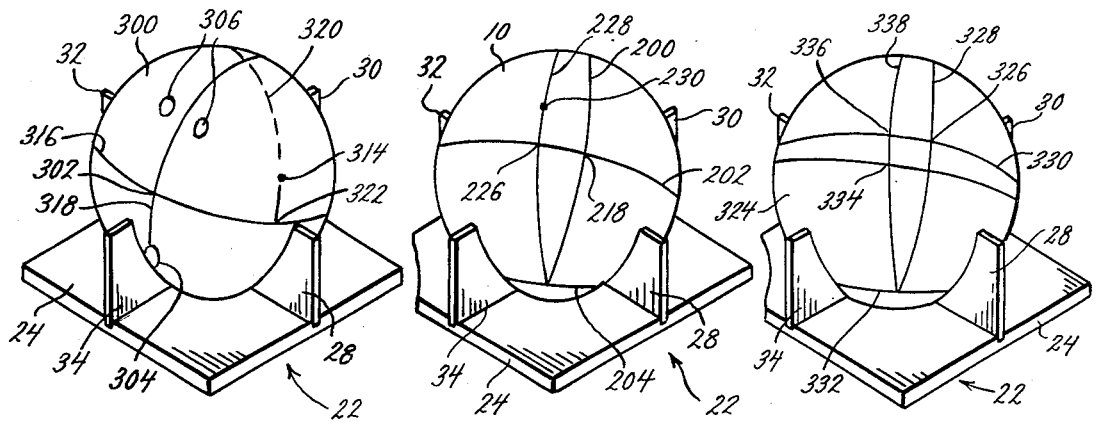
FIG. 20 is a developmental perspective illustrating the development of a relationship between a center-of-palm and an axis of roll.
FIG. 21 is a developmental perspective illustrating the development of a relationship between an initial MRP and a new MRP to achieve dynamic balance on a previously undrilled bowling ball.
FIG. 23 is a developmental perspective illustrating the development of a relationship between a TRP and an ARP.

As in EXAMPLE I a bowling ball of EXAMPLE II is placed in the ball cradle as shown in FIG. 3. The semicircular template 44 is placed across the ball as illustrated in FIGS. 3, 4, 5 and 7. The next step requires adjusting the position of the bowling ball in the cradle by means of the ball bearing support 26 in order to place the MRP on top of the ball, but only for convenience. It is already understood that an arbitrary TRP may be used instead of the MRP. Referring now to FIG. 21, a first perpendicular arc 200 and second perpendicular arc 202 are located on the surface of the bowling ball. In EXAMPLE II first intersection point 218 corresponds to the MRP. Unless otherwise indicated some reference characters, common to the description of each described embodiment, will be repeated.

The second perpendicular arc 202 is located by placing a semicircular template 44 against the other wings of the cradle and then drawing the second perpendicular arc using shoulder 46 in order to place the arc on the center line of the wings as illustrated in the drawings. A great circle 204 is then located and marked on the surface of the bowling ball by means of circular template 48 resting on top edges 84 of wings 28, 30, 32 and 34. It should be noted that the arcs and great circle can be used to aid in the positioning of the bowling ball in the dodo scale for weighing the bowling ball when determining the relative side weight, relative finger weight and relative top weight of the bowling ball.

When the relative weights are measured, the driller is ready to determine the first and second coordinates. In order to accomplish this the driller uses the pocket computer in the same or similar fashion as previously described.

Switch 118 is placed in the RUN position. Referring now to TABLE II, LINES 0-2 illustrate the initial input. The input of LINE 2 indicates that a new, undrilled bowling ball is being used. The measured weights are input in LINES 3-8 and at LINES 9 and 10 it is indicated to the operating system that the driller will determine the desired imbalance weights which are then input in LINES 11-16.

At LINES 17, 18 the driller inputs the span of the hand of the bowler and then indicates in LINES 19, 20 whether or not grips will be placed in the finger and/or grip holes since the weight of the grips affects the determination of the final desired weight imbalance selected by the bowler. Grips may be used in any or all of the grip holes, however, if at least one grip will be used the driller should input "Y" at LINE 20. Finger sizes are input in LINES 21-26 and ball weight is input at LINES 27, 28.

LINE 29 indicates a pause during which a signal such as a short beep may be provided to indicate that the operating system was unable to make the desired determinations as originally specified. The following disclosure of one embodiment of the operating system further discloses how the operating system continues the desired determinations in this situation. It will be understood that the number of beeps generally indicates the number of iterations required if a determination is possible.

As in EXAMPLE I LINES 30-37 give the first coordinate (LINE 32) and second coordinate (LINE 36).

After providing the first and second coordinates, the operating system determines the depth to which the thumb and finger grip holes must be drilled in order to remove the amount of material necessary to provide the desired weight imbalance as input in LINES 11-16.

TABLE II

| Line 0  | DRILLER: RUN [E]           |
|---------|----------------------------|
| Line 1  | COMPUTER: N)EW OR D)RILLED ? |
| Line 2  | DRILLER: N [E]             |
| Line 3  | C: SIDE WT. NOW?           |
| Line 4  | D: 0 [E]                   |
| Line 5  | C: FING. WT. NOW?          |
| Line 6  | D: .1 [E]                  |
| Line 7  | C: TOP WT.?                |
| Line 8  | D: 3.4 [E]                 |
| Line 9  | C: Y)OU OR COMP.?          |
| Line 10 | D: Y [E]                   |
| Line 11 | C: DES. SIDE WT.?          |
| Line 12 | D: .8 [E]                  |
| Line 13 | C: DES. FING. WT.?         |
| Line 14 | D: .2 [E]                  |
| Line 15 | C: DES. TOP WT.?           |
| Line 16 | D: .3 [E]                  |
| Line 17 | C: SPAN?                   |
| Line 18 | D: 4 [SPC] ⅜ [E]           |
| Line 19 | C: G)RIPS -- N)O GRIPS?    |
| Line 20 | D: N [E]                   |
| Line 21 | C: MID. FINGER SIZE?       |
| Line 22 | D? 15/16 [E]               |
| Line 23 | C: RING FINGER SIZE?       |
| Line 24 | D? 13/16 [E]               |
| Line 25 | C: THUMB SIZE?             |
| Line 26 | D: 1 [SPC] 1/64 [E]        |
| Line 27 | C: BALL WT.?               |
| Line 28 | D: 15.76 [E]               |
| Line 29 | C: BEEP                    |
| Line 30 | C: GO HORIZ.               |
| Line 31 | D: [E]                     |
| Line 32 | C: −1. IN.                 |
| Line 33 | D: [E]                     |
| Line 34 | C: GO VERT.                |
| Line 35 | D: [E]                     |
| Line 36 | C: 1./8. IN.               |
| Line 37 | D: [E]                     |
| Line 38 | C: THUMB DEPTH             |
| Line 39 | D? [E]                     |
| Line 40 | C: 3. AND 3./16. IN.       |
| Line 41 | D: [E]                     |
| Line 42 | C: MID. FING. DEPTH        |
| Line 43 | D: [E]                     |
| Line 44 | C: 1. AND 3./8. IN.        |
| Line 45 | D: [E]                     |
| Line 46 | C: RING FING. DEPTH        |
| Line 47 | D: [E]                     |
| Line 48 | C: 2. AND 1./16. IN.       |
| Line 49 | D: [E]                     |
| Line 50 | C: —                       |

Referring again to FIG. 21, second intersection point 226 may be located by measuring 1 inch along arc 202 to the left of the first intersection point 218, that is, in the negative direction. The second coordinate is measured along a third arc 228 that passes through both intersections of arc 200 and great circle 204 and the point 1 inch to the negative side of the first intersection point. The positive ⅛ inch of the second coordinate is measured along third arc 228 in order to determine the location of the third intersection point 230 corresponding to the center of palm or ARP of the bowling ball such that the bowling ball has the desired weight imbalance when the finger and thumb grip holes are drilled as specified.

EXAMPLE III

EXAMPLE III illustrates the use of the present invention to accurately determine the location of an ARP or center-of-palm of a new, preferably undrilled bowling ball in order to drill finger and thumb grip holes such that the bowling ball will be dynamically balanced. This is accomplished in part by transferring from a previously drilled bowling ball to a new bowling ball weight differences that will create dynamic balance and that are determined by the position of a ball track on the previously drilled bowling ball. The steps of transferring the weight differences from the existing bowling ball to the new bowling ball will now be described.

Referring now by characters of reference to FIGS. 16-18 a previously drilled bowling ball 300 is illustrated. Bowling ball 300 is shown in ball cradle 22. The bowling ball includes a center-of-palm 302 established with respect to a thumb grip hole 304 and a pair of finger grip holes 306.

In order to locate an existing ball track 308 the driller may take one of the bowler's bowling balls 300 and have the bowler roll the bowling ball on a bowling alley. The bowler's instructions are to roll the bowling ball consistent with his or her normal delivery. It is desirable but not essential that the bowling alley used have sufficient oil so that the bowling ball will pick up oil from the bowling alley and mark the existing ball track 308 on the surface of bowling ball 300. If the bowling alley is only lightly oiled, then a crayon or piece of chalk may be used to mark the ball track on the bowling ball. If a bowling ball has been used for a substantial period of time, then scuff marks will probably appear on the ball track, thereby eliminating the need to mark the ball track with oil from the bowling alley.

Next, placing the bowling ball 300 in ball cradle 22 with the ball track 308 located in the lower hemisphere of the bowling ball puts ball track 308 next to reference scales 36, 38, 40 and 42. By adjusting the position of bowling ball 300 in ball cradle 22 the driller may orient the bowling ball such that the ball track is adjacent corresponding planar reference points on the reference scales.

After the ball track is properly aligned in the cradle, the steps of the present invention continue by placing template 44 over the bowling ball and in cooperative association with pairs of wings 28, 32 and 30, 34, marking third arc 310 and fourth arc 312. The arcs intersect at point 314 on the axis of roll. The axis of roll is an imaginary line that passes through the center of the circle formed by ball track 308 and perpendicular to a plane defined by the ball track. It will be understood that there is another point similar to 314 on the opposite side of the bowling ball.

The next series of steps requires developing a fifth arc 316 and a sixth arc 318. The two arcs are perpendicular and their point of intersection is defined by the center-of-palm 302 of the existing bowling ball.

Rotating the bowling ball until the grip holes are on top of the bowling ball allows the center-of-palm to be located on the surface of bowling ball 300. The center-of-palm 302 may be defined by the intersection of two perpendicular arcs 316 and 318. Arc 316 is located halfway between the finger and thumb grip holes. Arc 318 is located halfway between the finger grip holes 306 and splits the thumb grip hole 304 into equal halves. It will be understood that ball cradle 22 may be readily used to locate and mark arcs 316 and 318. As a practical matter a driller may have left a small mark on a bowling ball's surface when originally drilling the grip holes that corresponds to center-of-palm 302. It will be understood from the foregoing description that this mark may be used to conveniently mark arcs 316 and 318 with the aid of cradle 22.

With reference to FIGS. 20 and 23 it will now be described how the location of the axis of roll intersection point 314 is related to center-of-palm 302 for the purpose of drilling a new bowling ball such that the new bowling ball is dynamically balanced. Referring now by characters of reference to FIG. 20, bowling ball 300 includes a center-of-palm 302 located at the center of thumb grip hole 304 and finger grip holes 306. The existing ball track 308, third arc 310 and fourth arc 312 are not shown in FIG. 20. The axis of roll intersection point 314, fifth arc 316 and sixth arc 318 are illustrated in FIG. 20.

In order to determine horizontal and vertical measurements between intersection point 314 and center-of-palm 302 of bowling ball 300, the driller, preferably with the use of cradle 22 and at least two opposing wings and semicircular template 44, locates a seventh arc 320 on the surface of the bowling ball. The arc 320 is perpendicular to arc 316.

Figure 19:
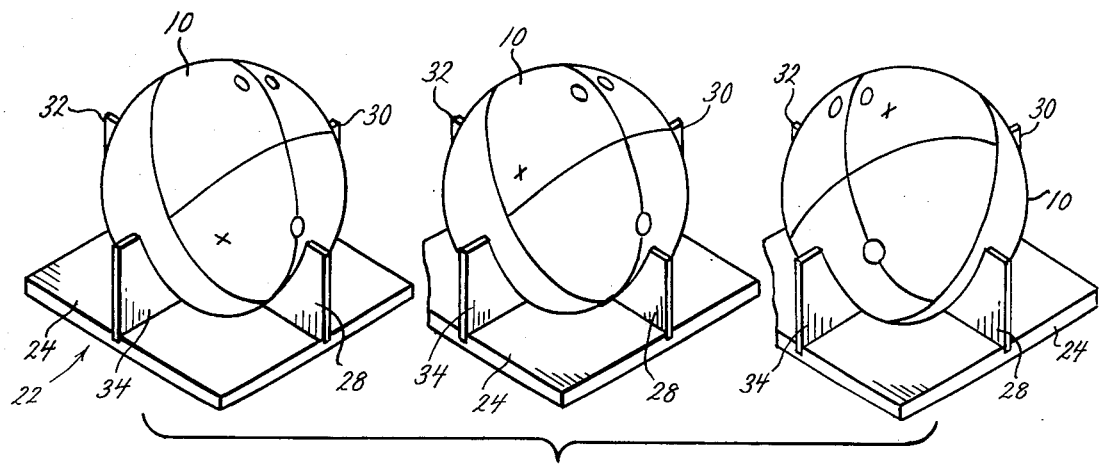
FIG. 19 is a developmental perspective of three additional possibilities for the relationship between a center-of-palm and an axis of roll.

Applying the horizontal and vertical system previously described it will be understood that intersection point 314 is positive with respect to both the horizontal and vertical direction. Reference is made to FIG. 19 and TABLE IA to illustrate that the horizontal and vertical system established for EXAMPLES I and II applies to EXAMPLE III as well as all of the preferred embodiments of the present invention. The previously described horizontal and vertical component system is an integral part of the described embodiment of the present invention. It will be understood that equivalent component system may be developed and applied and still be within the scope of the present invention.

Arc 320 intersects arc 316 at intersection point 322. The horizontal component or dimension is measured as a first distance from center-of-palm 302 to intersection point 322 along arc 316. The vertical component or dimension is measured as a second distance from intersection point 322 to axis of roll 314 along arc 320.

In order to further understand the relationship between the arcs marked on the bowling ball in EXAMPLE III it should be understood that arc 320 intersects arc 318 at the point arc 318 would intersect a great circle if the great circle were also perpendicular to both arcs 316 and 318.

The steps of the present invention to dynamically balance a new ball 324 will now be described in EXAMPLE III. It will be understood that a bowling ball may be dynamically balanced by concentrating a desired imbalance as axis weight along an axis of roll. It will be assumed for the purposes of EXAMPLE III that bowling ball 324 has the following characteristics that have already been determined in the manner described above. The existing relative weights of bowling ball 324 as measured by a dodo scale are assumed to be 0.1 ounce side weight, −0.2 ounce finger weight and 2.5 ounce top weight. The horizontal distance from center-of-palm 302 to intersection point 322 is 5¼ inches and the vertical distance from center-of-palm to point 314 as measured between intersection point 322 to point 314 along arc 320 is ½ inch. As previously discussed both of these dimensions are in a positive direction.

Taking into account the necessary requirements for drilling thumb and grip holes in bowling ball 324 it will be assumed in EXAMPLE III that grips will not be used and that the bowler has a hand span of 4⅜ inches.

In the present example the bowler has requested that the operating system of the preferred invention provide the final relative weights to dynamically balance the bowling ball and further that the finger and thumb grip holes be located for drilling such that eighty percent (80%) of the maximum weights allowed by the American Bowling Congress will be used. Use of these options will illustrate other features of the operating system of the present invention.

TABLE III

| | |
|---|---|
| Line 0 | DRILLER: RUN [E] |
| Line 1 | COMPUTER: N)EW OR D)RILLED? |
| Line 2 | DRILLER: N [E] |
| Line 3 | C: SIDE WT. NOW? |
| Line 4 | D: .1 [E] |
| Line 5 | C: FING. WT. ? |
| Line 6 | D: −.2 [E] |
| Line 7 | C: TOP WT. ? |
| Line 8 | D: 2.5 [E] |
| Line 9 | C: Y)OU OR C)OMP. ? |
| Line 10 | D: C [E] |
| Line 11 | C: HORIZ. MEAS. TO AXIS? |
| Line 12 | D: 5 [SPC] ¼ [E] |
| Line 13 | C: VERT. MEAS. TO AXIS? |
| Line 14 | D: ½ [E] |
| Line 15 | C: END. SIDE WT. 1. |
| Line 16 | D: [E] |
| Line 17 | C: END. FINGER WT. 0.12 |
| Line 18 | D: [E] |
| Line 19 | C: END. TOP WT. 0.36 |
| Line 20 | D: [E] |
| Line 21 | C: WHAT % |
| Line 22 | D: 80 [E] |
| Line 23 | C: SPAN? |
| Line 24 | D? 4 [SPC] ⅜ [E] |
| Line 25 | C: G)RIPS -- N)O GRIPS? |
| Line 26 | D: N [E] |
| Line 27 | C: MID. FINGER SIZE? |
| Line 28 | D: 13/16 [E] |
| Line 29 | C: RING FINGER SIZE? |
| Line 30 | D: 11/16 [E] |
| Line 31 | C: THUMB SIZE? |
| Line 32 | D: 1 [E] |
| Line 33 | C: BALL WT. ? |
| Line 34 | D? 15.4 [E] |
| Line 35 | C: GO HORIZ. |
| Line 36 | D: [E] |
| Line 37 | C: −1. AND 3./16. IN. |
| Line 38 | D: [E] |
| Line 39 | C: GO VERT. |
| Line 40 | D: [E] |
| Line 41 | C: −1./2. IN. |
| Line 42 | D: [E] |
| Line 43 | C: THUMB DEPTH |
| Line 44 | D: [E] |
| Line 45 | C: 2. AND 3./16. IN. |
| Line 46 | D: [E] |
| Line 47 | C: MID. FING. DEPTH |
| Line 48 | D: [E] |
| Line 49 | C: 1. AND 1./2. IN. |
| Line 50 | D: [E] |
| Line 51 | C: RING FING. DEPTH |
| Line 52 | D: [E] |
| Line 53 | C: 2. AND 3./8. IN. |
| Line 54 | D: [E] |
| Line 55 | C: — |

As previously described switch 118 of pocket computer 112 is switched to the RUN position and the word RUN is typed on alphabetical keypad 124 and then the ENTER button is pushed in order to start the operating system as shown on LINE 0 of TABLE III.

LINES 1 and 2 establish that the bowling ball will be a new, previously undrilled bowling ball. A previously drilled and subsequently plugged bowling ball would require the same steps. A plugged bowling ball will be understood to mean a previously drilled bowling ball in which the grip holes and possibly a balance hole have been plugged up or filled in so as to provide a bowling ball with a relatively smooth surface.

The measured side weight, finger weight and top weight of the existing bowling ball is input at LINES 3-8.

LINES 9 and 10 allow the user to choose the option in which the operating system computes the maximum weights available under the American Bowling Congress regulations. In EXAMPLE III the user has chosen the option "C" in which maximum weights will be determined in accordance with American Bowling Congress regulations. LINES 11-14 allow the user to input the measured distances on bowling ball 300 between the center-of-palm 302 and axis of roll intersection point 314.

A TRP 326 was located on bowling ball 324 by the driller in a similar fashion to EXAMPLES I and II. Perpendicular arcs 328 and 330 and great circle 332 were located, as in the previous examples, thereby dividing bowling ball 324 such that existing side weight, finger weight and top weight relative to TRP 326 could be determined from a dodo scale and input at LINES 15-20 in TABLE III.

At LINES 21, 22 the user indicates the percentage of the maximum weight imbalance desired and in the present example eighty percent (80%) of the maximum has been chosen as indicated by the input at LINE 22.

LINES 23-32 indicate the input relative to the span of the bowler's hand and the size of the bowler's fingers for determining the thumb and grip hole locations. As in the previous examples no grips have been indicated at LINE 26 in response to the output at LINE 25 and therefore the weights of the grips do not need to be considered by the operating system when determining the final location of the ARP and thumb and grip hole sizes and grips for new bowling ball 324 based upon the ball track developed from the bowler's existing ball 300.

The weight of ball 324 is input at LINE 34 in response to the query of LINE 33.

LINES 35 through 55 provide the necessary information to determine the ARP of new bowling ball 324 and the required depths at which the thumb and finger grip holes must be drilled in order to concentrate the desired weight imbalance at a corresponding axis of roll in new bowling ball 324 such that the new bowling ball 324 is dynamically balanced.

Referring now to FIG. 23, the following steps use the output from LINES 35 to 42 to locate ARP 334 of new bowling ball 324. Both the horizontal and vertical components are negative. Therefore, the driller measures 1 3/16 inches to the left of TRP 326 along arc 330 to locate intersection point 336 and ½ inch in the negative direction along an arc 338 to locate ARP 334. Arc 338 is located on the outer surface of bowling ball 324 such that arc 338 is perpendicular to arc 330. This will result in arc 338 and arc 328 intersecting great circle 332 at the same points. Arc 338 may be constructed with the aid of ball cradle 22 as previously described.

ARP 334 corresponds to a center-of-palm for new bowling ball 324 such that finger and grip holes drilled in accordance with the output of LINES 43 through 54 will result in the new bowling ball 324 being dynamically balanced.

EXAMPLE IV

EXAMPLE IV illustrates the use of the present invention to accurately determine the location of a balance hole and depth of the balance hole on a previously drilled bowling ball such that the bowling ball conforms to the bowler's imbalance specifications. EXAMPLE IV illustrates balancing a bowling ball to user prescribed final weight differences.

In EXAMPLE IV the bowler desires to have final weights of 1 ounce side weight, 0.3 ounces finger weight and 0.15 ounces top weight. The existing weight differences as measured by a dodo scale are 0 ounces side weight, 0.2 ounce finger weight and 2.1 ounce top weight.

Referring now by characters of reference to FIG. 24, there are two options available to the driller when performing the steps of the present invention on a previously drilled bowling ball 400, either the bowler or the operating system loaded in the pocket computer may determine the weight imbalance. In EXAMPLE IV the bowler selects a desired weight imbalance and the operating system and pocket computer disclosed herein are used to determine the location and depth of the balance hole. The other option is disclosed in EXAMPLE V below.

Initially two perpendicular arcs, a first arc and a second arc, 402 and 404 are located on the surface of bowling ball 400. The arcs are located and placed on the bowling ball as previously described using ball cradle 22, the wings and semicircular template. A first reference point or TRP 406 is located by arcs 402 and 404. A great circle 414 is located using the circle template 48. Bowling ball 400 is weighed in a dodo scale and the relative weights are determined generally in the same manner as disclosed and described in the previous Examples and description.

TABLE IV

| Line 0 | DRILLER: RUN[E] |
|---|---|
| Line 1 | COMPUTER: N)EW OR D)RILLED? |
| Line 2 | DRILLER: D[E] |
| Line 3 | C: SIDE WT. NOW? |
| Line 4 | D: O[E] |
| Line 5 | C: FING. WT.? |
| Line 6 | D: .2[E] |
| Line 7 | C: TOP WT.? |
| Line 8 | D: 2.1[E] |
| Line 9 | C: Y)OU OR C)OMP.? |
| Line 10 | D: Y[E] |
| Line 11 | C: DES. SIDE WT.? |
| Line 12 | D: 1[E] |
| Line 13 | C: DES. FING. WT.? |
| Line 14 | D: .3[E] |
| Line 15 | C: DES. TOP WT.? |
| Line 16 | D: .15[E] |
| Line 17 | C: GO HORIZ. |
| Line 18 | D: [E] |
| Line 19 | C: −1. AND 1./16. IN. |
| Line 20 | D: [E] |
| Line 21 | C: GO VERT. |
| Line 22 | D: [E] |
| Line 23 | C: −3./16. IN. |
| Line 24 | D: [E] |
| Line 25 | C: REMOVE 2.19 OUNCES |
| Line 26 | D: [E] |
| Line 27 | C: — |

Referring now to TABLE IV the driller starts the operating system as indicated at LINE 0 and as previously described. LINES 1 and 2 refer to the appropriate input for the situation in which a drilled ball is being balanced. The existing side weight, finger weight and top weight are measured by the dodo scale and the relative weights input as illustrated in LINES 3-8. LINES 9 and 10 indicate that the driller or the bowler will be determining the desired weight differences which are input in LINES 11-16.

The operating system of the present invention makes the necessary determinations and then, as represented in LINES 17-24, identifies the location of a balance hole using the previously described horizontal and vertical component system with a first coordinate and a second coordinate. Finally, LINES 25 and 26 indicate, but do not equal, the necessary weight of material that must be removed from the just determined location of the balance hole in order to provide the existing bowling ball with the new final weight differences.

Once the location of another intersection point or balance hole and its depth have been determined, the driller measures horizontally along arc 404 and 1 1/16 inches in the negative direction to coordinate 416 starting at the center-of-palm 406 of bowling ball 400. The next step requires the construction of arc 418 through coordinate 416 and perpendicular to arc 404 similarly to the arcs constructed in the preceding examples and description. The driller then measures along arc 418 in the negative direction 3/16 inch. The driller has now located balance hole 420.

In order to find the combination of drill bit diameter and hole depth the driller may use TABLE IVA. It will be understood that the contents of TABLE IVA may be stored in and accessed from a computer with sufficient memory.

TABLE IVA

Amount to Remove (oz.)

Depth of Balance Hole (inches)
Ball Weight = 8

| Bit Size | 0.1 | 0.2 | 0.3 | 0.4 | 0.5 |
|---|---|---|---|---|---|
| 3/8 in. | 1⅞ to 2⅞ | | | | |
| 1/2 in. | 1 to 1⅝ | 2½ to 3½ | | | |
| 5/8 in. | ⅝ to 1 | 1⅜ to 2 | 2 to 3 | | |
| 3/4 in. | ½ to ¾ | 1 to 1⅜ | 1⅜ to 2⅛ | 1⅞ to 2⅞ | |
| 7/8 in. | ⅜ to ½ | ¾ to 1 | 1 to 1½ | 1⅜ to 2⅛ | 1¾ to 2⅝ |
| 1 in. | ¼ to ⅜ | ½ to ¾ | ¾ to 1¼ | 1 to 1⅝ | 1⅜ to 2 |
| 1⅛ in. | ¼ to ⅜ | ⅜ to ⅝ | ⅝ to 1 | ⅞ to 1¼ | 1 to 1⅝ |
| | 0.6 | 0.7 | 0.8 | 0.9 | 1.0 |

| Bit Size | | | | | |
|---|---|---|---|---|---|
| 7/8 in. | 2¼ to 3¼ | | | | |
| 1 in. | 1⅝ to 2⅝ | 1⅞ to 2¾ | 2¼ to 3¼ | | |
| 1⅛ in. | 1¼ to 1⅞ | 1½ to 2¼ | 1⅝ to 2½ | 1⅞ 2⅞ | 2¼ to 3¼ |
| 1¼ in. | 1 to 1½ | 1¼ to 1¾ | 1⅜ to 2 | 1½ to 2¼ | 1¾ to 2½ |
| | 1.1 | 1.2 | 1.3 | 1.4 | 1.5 |

| Bit Size | | | | | |
|---|---|---|---|---|---|
| 1⅛ in. | 2¼ to 3½ | | | | |
| 1¼ in. | 1⅞ to 2¾ | 2 to 3 | 2¼ to 3½ | | |

Depth of Balance Hole (inches)
Ball Weight = 10

| Bit Size | 0.1 | 0.2 | 0.3 | 0.4 | 0.5 |
|---|---|---|---|---|---|
| 3/8 in. | 1½ to 2¼ | | | | |
| 1/2 in. | ⅞ to 1¼ | 1⅜ to 2½ | | | |
| 5/8 in. | ½ to ⅞ | 1⅛ to 1⅝ | 1⅝ to 2⅜ | 2¼ to 3¼ | |
| 3/4 in. | ⅜ to ⅝ | ¾ to 1⅛ | 1⅛ to 1¾ | 1½ to 2¼ | 1⅞ to 2⅞ |
| 7/8 in. | ¼ to ⅜ | ½ to ⅞ | ⅞ to 1¼ | 1⅛ to 1⅝ | 1⅜ to 2⅛ |
| | 0.6 | 0.7 | 0.8 | 0.9 | 1.0 |

| Bit Size | | | | | |
|---|---|---|---|---|---|
| 3/4 in. | 2¼ to 3⅜ | | | | |
| 7/8 in. | 1⅝ to 2½ | 1⅞ to 2⅞ | 2¼ to 3⅜ | | |
| 1 in. | 1¼ to 1⅞ | 1½ to 2¼ | 1¾ to 2½ | 1⅞ to 2⅞ | 2¼ to 3½ |
| 1⅛ in. | 1 to 1½ | 1¼ to 1⅞ | 1⅜ to 2 | 1½ to 2¼ | 1⅝ to 2½ |
| 1¼ in. | ⅞ to 1¼ | 1 to 1⅜ | 1⅜ to 1⅝ | 1¼ to 1⅞ | 1⅜ to 2 |
| | 1.1 | 1.2 | 1.3 | 1.4 | 1.5 |

| Bit Size | | | | | |
|---|---|---|---|---|---|
| 1 in. | 2¾ to 3½ | | | | |
| 1⅛ in. | 1⅜ to 2¾ | 2 to 3 | 2¼ to 3½ | | |
| 1¼ in. | 1½ to 2½ | 1⅞ to 2½ | 1¾ to 2⅝ | 1⅞ to 2⅞ | 2 to 3 |
| | 1.6 | 1.7 | 1.8 | 1.9 | 2.0 |

TABLE IVA-continued

Amount to Remove (oz.)

| Bit Size | | | | | |
|---|---|---|---|---|---|
| 1¼ in. | 2⅜ to 3¼ | 2¼ to 3½ | | | |

Depth of Balance Hole (inches)
Ball Weight = 12

| | 0.1 | 0.2 | 0.3 | 0.4 | 0.5 |
|---|---|---|---|---|---|

| Bit Size | | | | | |
|---|---|---|---|---|---|
| 3/8 in. | 1¼ to 1⅞ | | | | |
| 1/2 in. | ¾ to 1 | 1⅜ to 2¼ | 2⅛ to 3⅛ | | |
| 5/8 in. | ½ to ⅞ | ⅞ to 1⅜ | 1⅜ to 2 | 1¾ to 2⅝ | 2¼ to 3¼ |
| 3/4 in. | ⅜ to ½ | ⅝ to 1 | 1 to 1⅜ | 1¼ to 1⅞ | 1⅝ to 2⅜ |
| 7/8 in. | ¼ to ⅜ | ½ to ¾ | ¾ to 1 | ⅞ to 1⅜ | 1⅛ to 1¾ |
| | 0.6 | 0.7 | 0.8 | 0.9 | 1.0 |

| Bit Size | | | | | |
|---|---|---|---|---|---|
| 3/4 in. | 1⅞ to 2⅞ | 2¼ to 3¼ | | | |
| 7/8 in. | 1⅜ to 2¼ | 1⅝ to 2⅝ | 1⅞ to 2⅞ | 2¼ to 3¼ | 2¼ to 3½ |
| 1 in. | 1 to 1⅝ | 1¼ to 1⅞ | 1⅜ to 2¼ | 1⅝ to 2⅝ | 1⅞ to 2⅝ |
| 1⅛ in. | ⅞ to 1¼ | 1 to 1½ | 1⅛ to 1⅝ | 1¼ to 1⅞ | 1⅜ to 2¼ |
| 1¼ in. | ⅝ to 1 | ¾ to 1⅛ | ⅞ to 1⅜ | 1 to 1½ | 1⅛ to 1¾ |
| | 1.1 | 1.2 | 1.3 | 1.4 | 1.5 |

| Bit Size | | | | | |
|---|---|---|---|---|---|
| 1 in. | 1⅞ to 2⅞ | 1⅞ to 2¾ | 2 to 3 | 2⅛ to 3⅛ | 2¼ to 3⅜ |
| 1⅛ in. | 1⅜ to 2 | 1⅜ to 2¼ | 1½ to 2⅜ | 1⅝ to 2½ | 1⅞ to 2¼ |
| 1¼ in. | 1¼ to 1⅝ | 1¼ to 1¾ | 1¼ to 1⅞ | 1⅜ to 2 | 1½ to 2¼ |
| | 1.6 | 1.7 | 1.8 | 1.9 | 2.0 |

| Bit Size | | | | | |
|---|---|---|---|---|---|
| 1⅛ in. | 1⅞ to 2⅞ | 2 to 3 | 2¼ to 3¼ | 2¼ to 3⅜ | |
| 1¼ in. | 1½ to 2⅜ | 1⅝ to 2⅝ | 1⅞ to 2⅝ | | 1⅞ to 2⅞ |

Depth of Balance Hole (inches)
Ball Weight = 15

| | 0.1 | 0.2 | 0.3 | 0.4 | 0.5 |
|---|---|---|---|---|---|

| Bit Size | | | | | |
|---|---|---|---|---|---|
| 1/4 in. | 2¼ to 3⅜ | | | | |
| 3/8 in. | 1 to 1½ | 2 to 3 | | | |
| 1/2 in. | ⅝ to ⅞ | 1¼ to 1⅞ | 1⅜ to 2½ | 2¼ to 3⅜ | |
| 5/8 in. | ⅜ to ½ | ¾ to 1⅛ | 1⅛ to 1⅝ | 1½ to 2¼ | 1⅞ to 2¾ |
| 3/4 in. | ¼ to ⅜ | ½ to ¾ | ¾ to 1⅛ | 1 to 1½ | 1¼ to 1⅞ |
| | 0.6 | 0.7 | 0.8 | 0.9 | 1.0 |

| Bit Size | | | | | |
|---|---|---|---|---|---|
| 3/4 in. | 1½ to 2¼ | 1¾ 2⅝ | 2 to 3 | 2¼ to 3⅜ | |
| 7/8 in. | 1⅛ to 1⅝ | 1¼ to 1⅞ | 1½ to 2¼ | 1⅝ to 2½ | 1⅞ to 2¾ |
| 1 in. | ⅞ to 1¼ | 1 to 1½ | 1¼ to 1¾ | 1¼ to 1⅞ | 1⅜ to 2⅜ |
| 1⅛ in. | ⅝ to 1 | ¾ to 1¼ | ⅞ to 1⅜ | 1 to 1½ | 1⅛ to 1⅝ |
| 1¼ in. | ½ to ⅞ | ⅝ to 1 | ¾ to 1¼ | ⅞ to 1¼ | ⅞ to 1⅜ |
| | 1.1 | 1.2 | 1.3 | 1.4 | 1.5 |

| Bit Size | | | | | |
|---|---|---|---|---|---|
| 7/8 in. | 2 to 3 | 2¼ to 3¾ | | | |

TABLE IVA-continued

| | Amount to Remove (oz.) | | | | |
|---|---|---|---|---|---|
| 1 in. | 1½ to 2⅜ | 1⅞ to 2½ | 1⅞ to 2¾ | 2 to 3 | 2⅜ to 3⅛ |
| 1⅛ in. | 1¼ to 1⅞ | 1⅜ to 2 | 1½ to 2¼ | 1½ to 2⅜ | 1⅝ to 2½ |
| 1¼ in. | 1 to 1½ | 1⅛ to 1⅝ | 1⅛ to 1¾ | 1⅜ to 1⅞ | 1⅞ to 2 |
| | 1.6 | 1.7 | 1.8 | 1.9 | 2.0 |

| Bit Size | | | | | |
|---|---|---|---|---|---|
| 1⅛ in. | 1¾ to 2⅝ | 1⅞ to 2⅞ | 2 to 3 | 2⅛ to 3⅛ | 2¼ to 3⅜ |
| 1¼ in. | 1½ to 2¼ | 1½ to 2¼ | 1⅝ to 2½ | 1¾ to 2⅝ | 1¾ to 2¾ |

Depth of Balance Hole (inches)
Ball Weight = 16

| | 0.1 | 0.2 | 0.3 | 0.4 | 0.5 |
|---|---|---|---|---|---|
| Bit Size | | | | | |
| ¼ in. | 2½ to 3½ | | | | |
| ⅜ in. | 1 to 1⅞ | 1⅞ to 2⅞ | | | |
| ½ in. | ½ to ¾ | 1 to 1⅝ | 1⅝ to 2⅝ | 2⅛ to 3⅛ | |
| ⅝ in. | ⅜ to ½ | ⅝ to 1 | 1 to 1½ | 1⅜ to 2 | 1¾ to 2¼ |
| ¾ in. | ¼ to ⅜ | ½ to ¾ | ¾ to 1 | 1 to 1⅜ | 1⅛ to 1¾ |
| | 0.6 | 0.7 | 0.8 | 0.9 | 1.0 |
| Bit Size | | | | | |
| ¾ in. | 1⅜ to 2⅛ | 1⅝ to 2½ | 1⅞ to 2⅞ | 2⅛ to 3⅛ | |
| ⅞ in. | 1 to 1½ | 1¼ to 1⅞ | 1⅜ to 2⅛ | 1½ to 2⅝ | 1¾ to 2⅝ |
| 1 in. | ¾ to 1¼ | ⅞ to 1⅜ | 1 to 1⅝ | 1¼ to 1¾ | 1⅜ to 2 |
| 1⅛ in. | ⅝ to 1 | ¾ to 1⅛ | ⅞ to 1¼ | 1 to 1⅜ | 1 to 1⅝ |
| 1¼ in. | ½ to ¾ | ⅝ to ⅞ | ⅝ to 1 | ¾ to 1⅛ | ⅞ to 1¼ |
| | 1.1 | 1.2 | 1.3 | 1.4 | 1.5 |
| Bit Size | | | | | |
| ⅞ in. | 1⅞ to 2⅞ | 2⅛ to 3⅛ | 2¼ to 3⅜ | | |
| 1 in. | 1½ to 2¼ | 1⅝ to 2⅜ | 1¾ to 2⅝ | 1⅞ to 2⅞ | 2 to 3 |
| 1⅛ in. | 1⅛ to 1¾ | 1¼ to 1⅞ | 1⅜ to 2 | 1½ to 2¼ | 1⅝ to 2⅝ |
| 1¼ in. | ⅞ to 1⅜ | 1 to 1½ | 1⅛ to 1⅝ | 1⅛ to 1¾ | 1¼ to 1⅞ |
| | 1.6 | 1.7 | 1.8 | 1.9 | 2.0 |
| Bit Size | | | | | |
| 1 in. | 2⅛ to 3⅛ | 2¼ to 3⅜ | | | |
| 1⅛ in. | 1⅝ to 2½ | 1¾ to 2⅝ | 1⅞ to 2⅞ | 2 to 3 | 2⅛ to 3⅛ |
| 1¼ in. | 1⅜ to 2 | 1½ to 2¼ | 1½ to 2¼ | 1⅝ to 2⅜ | 1¾ to 2½ |

The location of a balance hole has been determined by the present invention to be drilled at the located point 420 directly towards the center of the ball without any pitch and to the prescribed depth for the size drill bit chosen as indicated in TABLE IVA. In order to assure accuracy it is suggested that the driller take the hole to a depth of approximately the smaller of the ranges given on TABLE IVA and then weigh the ball to see if it has the desired weight differences. If necessary the driller may drill a little deeper. Generally, the correct depth will be in the middle of the ranges given in TABLE IVA. It will be understood that most depths not listed in TABLE IVA may be obtained from the Table by standard extrapolation methods.

EXAMPLE V

EXAMPLE V illustrates the use of the present invention to accurately determine the location of a balance hole and the depth of the balance hole on a previously drilled bowling ball in order that the bowling ball will have optimum weight differences determined by the operating system to achieve balance for all three sides (first side and second side, finger side and thumb side, top side and bottom side) of the bowling ball. In this embodiment the operating system selects the relative side weight, relative finger weight and relative top weight so as to concentrate the weight imbalance along the axis of roll. This is also referred to as axis weight. The bowler does not need to know that weight differences or relative weights are optimum for him or her.

Referring now by characters of reference to FIGS. 25-29 a previously drilled bowling ball 500 is illustrated. Bowling ball 500 is shown in ball cradle 22. The bowling ball includes a first reference point or center-of-palm 502 established with respect to a thumb grip hole 504 and a pair of finger grip holes 506 as previously described.

In order to locate an existing ball track 508 the driller takes bowling ball 500 and has the bowler roll the bowling ball on a bowling alley. The bowler's instructions are to roll the bowling ball consistently with his or her normal delivery. It is desirable but not essential that the bowling alley used has sufficient oil so that the bowling ball will pick up oil from the bowling alley and mark the existing ball track 508 on the surface of bowling ball 500. If the bowling alley is only lightly oiled, then a crayon or a piece of chalk may be used to mark the ball track on the bowling ball. If a bowling ball has been used for a substantial period of time then scuff marks will probably appear on the ball track, thereby eliminating the need to mark the ball track with oil from the bowling alley.

Next, placing the bowling ball 50 in ball cradle 22 with the ball track 508 located in the lower half of the hemisphere of the bowling ball puts the ball track 508 next to reference scales 36, 38, 40 and 42. By adjusting the position of bowling ball 500 in ball cradle 22 the driller may orient the bowling ball such that the ball track developed on the outer surface of the bowling ball 500 is adjacent corresponding planar reference marks.

After the ball track is properly aligned in the cradle the steps of the present invention continue by placing a template 44 over the bowling ball and in cooperative association with pairs of wings 28, 32 and 30, 34, marking an arc 510 and an arc 512 on the surface of bowling ball 500 as previously described. The arcs are located on the surface of the bowling ball so as to intersect at a point 514 where the axis of roll intersects the surface of bowling ball 500. The axis of roll corresponds to an imaginary line that passes through the center of the circle formed by ball track 508 and perpendicular to a plane defined by the ball track. It will be understood that there is another similar point on the opposite side of bowling ball 500.

The next steps require developing arc 516 and arc 518. These two arcs are perpendicular to each other and their point of intersections is defined by center-of-palm 502 of bowling ball 500.

Rotating the bowling ball until the grip holes are on top of the bowling ball allows the center-of-palm to be located on the surface of the bowling ball 500. The center-of-palm 502 may be defined by the intersection of two perpendicular arcs 516 and 518. Arc 516 is located halfway between the finger and thumb grip holes. Arc 518 is located halfway between the finger grip holes 506 and splits the thumb grip hole 504 into equal halves. It will be understood that ball cradle 22 may be readily used to located and mark arcs 516 and 518 on the surface of bowling ball 500. As a practical matter, a driller may leave a small mark on a bowling ball surface that corresponds to the center-of-palm for the thumb and finger grip holes previously drilled into the bowling ball. It will be understood from the foregoing description that this mark may be used to conveniently mark arcs 516 and 518 with the aid of cradle 22 and the wings and semicircular template 44.

With reference to FIGS. 28 and 29 it will now be described how the location of axis of roll intersection point 514 is related to center-of-palm 502 for the purpose of drilling a balance hole in bowling ball 500 such that the weight imbalance of the relative side weight, relative finger weight and relative top weight of bowling ball 500 is concentrated as axis weight along the axis of roll. Referring now by characters of reference to FIG. 28, the bowling ball 500 includes the center-of-palm 502 located at the center of thumb grip hole 504 and finger grip holes 506. Ball track 508, arc 510 and arc 512 are not shown in FIG. 28. The axis of roll intersection point 514, arc 516 and arc 518 are illustrated in FIG. 28.

In order to determine first and second coordinates corresponding to horizontal and vertical measurements between intersection point 514 and center-of-palm 502 of bowling ball 500, the driller, preferably with the use of cradle 22 and at least two opposing wings and semi-circular template 44, locates an arc 520 on the surface of the bowling ball 500. The arc 520 is perpendicular to arc 516.

Applying the horizontal and vertical system previously described it will be understood that intersection point 514 in EXAMPLE V is positive with respect to both the horizontal and vertical direction. Reference is made to FIGS. 15 and 19 and TABLE IA to illustrate that the horizontal and vertical system established in the preceding examples which also applies to EXAMPLE V.

Arc 520 intersects arc 516 at intersection point 522. The horizontal component or dimension is measured from center-of-palm 502 to intersection point 522 along arc 516. The vertical component or dimension is measured from intersection point 522 to axis of roll 514 along arc 520.

In order to further understand the relationship between the arcs marked on the surface of bowling ball 500 in EXAMPLE V it should be understood that arc 520 intersects arc 518 at the point arc 518 would intersect a great circle if the great circle were also perpendicular to both arcs 516 and 518. This is illustrated in FIG. 27 as great circle 526.

The steps of this embodiment of the present invention to concentrate the desired weight imbalance of a previously drilled ball along the axis of roll will now be described further in EXAMPLE V.

It will be assumed for the purposes of EXAMPLE V that bowling ball 500 has the following characteristics determined by means of measuring bowling ball 500 in a dodo scale and using arcs 516, 518 and great circle 526 in order to establish the relative finger weight, relative side weight, and relative top weight, respectively. The existing relative weights of bowling ball 500 as measured by the dodo scale are presumed to be 0.1 ounce side weight, −0.2 ounce finger weight and 2.3 ounce top weight. The horizontal distance from center-of-palm 502 to intersection point 522 has been measured to be 4⅞ inches and the vertical distance from the center-of-palm to the axis of roll 514 as measured between intersection point 522 to axis of roll 514 along arc 520 is ¾ inch. As previously discussed both of these dimensions are in a positive direction.

In the preferred embodiment illustrated in EXAMPLE V the operating system determines the final relative weights with respect to the axis of roll.

TABLE V

| Line 0 | DRILLER: RUN[E] |
|---|---|
| Line 1 | COMPUTER: N)EW OR D)RILLED? |
| Line 2 | DRILLED: D[E] |
| Line 3 | C: SIDE WT. NOW? |
| Line 4 | D: .1 [E] |
| Line 5 | FING. WT.? |

TABLE V-continued

| Line 6 | D: −.2 [E] |
|---|---|
| Line 7 | TOP WT.? |
| Line 8 | D: 2.3 [E] |
| Line 9 | C: Y)OU OR C)OMP.? |
| Line 10 | D: C [E] |
| Line 11 | C: HORIZ. MEAS. TO AXIS? |
| Line 12 | D; 4 [SPC] ⅞ [E] |
| Line 13 | C: VERT. MEAS. TO AXIS? |
| Line 14 | D: ¾ [E] |
| Line 15 | C: END. SIDE WT. 1. |
| Line 16 | D: [E] |
| Line 17 | C: END. FINGER WT. 0.19 |
| Line 18 | D: [E] |
| Line 19 | C: END. TOP WT. 0.47 |
| Line 20 | D: [E] |
| Line 21 | C: WHAT % |
| Line 22 | D: 50 [E] |
| Line 23 | C: GO HORIZ. |
| Line 24 | D: [E] |
| Line 25 | C: −13./16. IN. |
| Line 26 | D: [E] |
| Line 27 | C: GO VERT. |
| Line 28 | D: [E] |
| Line 29 | C: −5./8. IN. |
| Line 30 | D: [E] |
| Line 31 | C: REMOVE 2.13 OUNCES |
| Line 32 | D: [E] |
| Line 33 | C: — |

The pocket computer is used in the same fashion as in the previous examples and the driller starts the operating system by inputting the word RUN and the ENTER key as illustrated in LINE 0 of TABLE V.

LINES 1 and 2 illustrate the manner in which the driller indicates to the operating system that the bowling ball in question is a previously drilled bowling ball. The driller inputs the measured side weight, finger weight and top weight in LINES 3–8. LINES 9 and 10 indicate that the driller has chosen the option allowing the operating system to determine ending side weight, finger weight and top weight which it does and provides the weight values in LINES 15–20. At LINES 21, 22 the driller indicates that the user desires to use fifty percent (50%) of the determined side weight, finger weight and top weight for determining the location and depth of a second reference point corresponding to a second reference point corresponding to a new balance hole in a previously drilled ball in accordance with American Bowling Congress regulations. As in the previous examples the horizontal and vertical measurements are input and this is illustrated at LINES 11–14.

The operating system output is illustrated in LINES 23–32. For the present exaample, EXAMPLE V, it is found that the balance hole is located −13/16 of an inch in the horizontal direction and −⅝ of an inch in the vertical direction thereby placing the new balance hole in the quadrant illustrated in FIG. 19A. LINE 31 indicates that the driller must remove sufficient weight from the bowling ball at the identified location in order to create a weight difference of 2.13 ounces.

Referring now to FIG. 29, the horizontal dimension of −13/16 inch will be measured to the left of center-of-palm 502 along arc 516 thereby determining the location of a point 524. The vertical coordinate is measured along an arc 528 located through point 524 and perpendicular to arc 516. As in the previous examples, the ball cradle 22 and associated apparatus may be used to develop and mark arc 528 on the surface of bowling ball 500 as required. The intersection between arc 528 and great circle 526 coincides with the intersection between arc 518 and great circle 526.

The location of balance hole 530 may be determined by measuring $-\frac{3}{8}$ inch along arc 528 as illustrated in FIG. 29. The ball cradle 22 and associated apparatus may be used to measure the horizontal and vertical dimensions on bowling ball 500 as noted in the previous examples.

Creating a weight difference of 2.13 ounces will result in the relative weight imbalance of the bowling ball being concentrated along the axis of roll that is, as axis weight. TABLE IVA may be used to determine the depth and the diameter of the balance hole determined in EXAMPLE V.

If balance hole 530 intersects the ball track 508 or is located near thrumb grip hole 504 or finger grip hole 506, then the ball may have to be rebalanced. Alternatively, the driller may drill one or more of the grip holes deeper, re-weigh the bowling ball on the dodo scale for relative side weight, relative finger weight and relative top weight and rerun EXAMPLE V with new existing weights until the balance hole 530 can be drilled in bowling ball 500 without interfering with the ball track 508 or grip holes 504 or 506.

It will now be understand from the foregoing EXAMPLES I–V that the present invention incorporates certain theories regarding various weight relationships. These theories are incorporated into the operating system used by the pocket computer as disclosed in the preferred embodiment. A preferred embodiment of operating system source code is listed in TABLE VI, below.

TABLE VI

```
5:DIM Z(20): RADIAN :K
 =4.297:J=13.5
6:Z(6)=1: GOTO 400
12:INPUT "SIDE WT. NOW?
 ";S
14:INPUT "FING. WT. ?"
 ;F
16:INPUT "TOP WT. ? ";T
18:INPUT "Y)OU OR C)OMP
 .? ";N$
20:IF N$="Y" THEN 32
22:IF N$="C" THEN 188
24:GOTO 18
32:INPUT "DES. SIDE WT.
 ? ";R
34:INPUT "DES. FING. WT
 .? ";E
36:INPUT "DES. TOP WT.?
 ";V
38:I= SQR ((S−R) 2+(T−V
 ) 2+(F−E) 2)
40:X= ABS (S−R):Y= ABS
 (T−V):Z= ABS (F−E)
42:L=0:M=0
54:IF R=S THEN 72
56:IF F=E THEN 86
58:IF T=V THEN 96
59:M= +K* ATN (Z/ SQR (X
 *X+Y*Y))
60:IF S>R THEN 104
62:IF F>E THEN 114
64:M= −K* ATN (Z/ SQR (X
 2+Y 2))
66:IF T>V THEN 118
68:L= −J+(K* ATN (X/Y)):
 GOTO 254
72:IF F=E THEN 120
76:IF T=V THEN 126
78:IF T>V THEN 170
80:L=J: IF F>E THEN LET
 M=K* ATN (Z/Y): GOTO
 254
84:GOTO 172
86:IF T=V THEN 138
90:IF T>V THEN 142
92:IF S>R THEN 146

94:L= −J+K* ATN (X/Y):
 GOTO 254
96:IF S>R THEN 148
98:L= −J/2: IF F>E THEN
 154
102:M= −K* ATN (Z/X):
 GOTO 254
104:IF F>E THEN 156
106:M= −K* ATN (Z/ SQR (X
 2+Y 2))
108:IF T>V THEN 178
110:GOTO 146
114:IF T>V THEN 118
117:M=K* ATN (Z/ SQR (X*
 X+Y*Y)): GOTO 94
118:L= −K* ATN (X/Y):
 GOTO 254
120:IF T=V THEN 252
122:IF T<V THEN 166
124:GOTO 254
126:IF F<E THEN 168
128:M=J/2: GOTO 254
138:IF S>R THEN 176
140:L= −J/2: GOTO 254
142:IF S>R THEN 178
144:GOTO 118
146:L=J− K* ATN (X/Y):
 GOTO 254
148:L=J/2: IF F>E THEN 1
 54
152:GOTO 102
154:M=K* ATN (Z/X): GOTO
 254
156:M=K* ATN (Z/ SQR (X
 2+Y 2))
158:IF T>V THEN 178
160:GOTO 146
166:L=J: GOTO 254
168:M= −J/2: GOTO 254
170:IF F>E THEN 184
172:M= −K* ATN (Z/Y):
 GOTO 254
176:L=J/2: GOTO 254
178:L=K* ATN (X/Y): GOTO
 254

184:M=K* ATN (Z/Y): GOTO
 254
188:INPUT "HORIZ. MEAS.
 TO AXIS?";A$: GOSUB
 690:H=Z(16)
190:INPUT "VERT. MEAS. T
 O AXIS?";A$: GOSUB
 690:G=Z(16)
192:P= ABS (H):Q= ABS (G
 )
193:IF P<.32*K OR P>2.82
 *K THEN 212
194:IF H<0 THEN LET R= −1
195:IF H>=0 THEN LET R=1
196:IF P>J/2 THEN LET O=
 (J−P)/K: GOTO 198
198:O=P/K:V= ABS (R/ TAN
 (O))
200:IF (H<−J/2 OR H>J/2)
 THEN LET V= −1* ABS (
 V)
202:I= SQR (V*V+R*R)
205:W=Q/K: IF ABS (I*
 TAN (W))<=1 THEN 208
206:Z(1)= ABS (I* TAN (W
 )):R=R/Z(1):V=V/Z(1)
 :E=(G>0)−(G<=0):
 GOTO 380
208:IF G<0 THEN LET E= −I
 * TAN (W)
209:IF G>=0 THEN LET E=I
 * TAN (W): GOTO 380
212:IF P>J/2 THEN LET V=
 −3: GOTO 214
214:V=3: IF P>J/2 THEN
 LET O=(J−P)/K: GOTO
 216
216:O=P/K: IF H>0 THEN
 LET R=V* TAN (O):
 GOTO 218
217:R= −V* TAN (O)
218:I= SQR (V*V+R*R):W=Q
 /K:E=I* TAN (W)
224:IF E>1 THEN LET V=V/
 E: GOTO 216
```

```
184:M=K* ATN (Z/Y): GOTO
 254
188:INPUT "HORIZ. MEAS.
 TO AXIS? ";A$: GOSUB
 690:H=Z(16)
190:INPUT "VERT. MEAS. T
 O AXIS? ";A$: GOSUB
 690:G=Z(16)
192:P= ABS (H):Q= ABS (G
 )
193:IF P<.32*K OR P>2.82
 *K THEN 212
194:IF H<0 THEN LET R= −1
195:IF H>=0 THEN LET R=1
196:IF P>J/2 THEN LET O=

409:H=0: INPUT "RING FIN
 GER SIZE? ";A$:
 GOSUB 690:Z(3)=Z(16)
 : IF N$="G"THEN
 GOSUB 950:H=Z(16)
412:Q=0: INPUT "THUMB SI
 ZE?";A$: GOSUB 690:
 Z(4)=Z(16): IF N$="G
 " THEN GOSUB 950:Q=Z
 (16)
413:INPUT "BALL WT.? ";Z
 (8)
414:Z(0)=Z(0)+Z(2)/4+Z(3
 )/4+Z(4)/2
415:Z(6)=0:Z(7)=1
499:Z(20)= SQR (S*S+T*T)
 :L=(S−R)/Z(20)*K

706:IF Z(17)=0 AND Z(18)
 =0 THEN LET Z(16)=
 VAL (A$): RETURN
708:O= VAL ( LEFT$ (A$,Z
 (17))):W= VAL ( MID$
 (A$,Z(17)+1,3))
710:Z(1)= SGN ( VAL (A$)
 )* VAL ( RIGHT$ (A$,
 LEN (A$)−Z(18)))
711:Z(16)=0+W/Z(1):
 RETURN
750:Z(9)=(18.5− 168.39*(B
 +D)/( COS (Z(0)/8.6
 )/U 2/Z(8)): IF Z(9)
 <0 THEN GOTO 760
752:Z(9)=K− SQR (Z(9)):
 RETURN
```

TABLE VI-continued

```
(J-P)/K: GOTO 198              500:Z(20)= SQR (T*T-F*F)       760:Z(6)=2: BEEP 1:I=.9*
198:O=P/K:V= ABS (R/ TAN       :M=(F-E)/Z(20)*K:I=            I: GOTO 602
(O))                           SQR (T*T+S*S+F*F-R*R           800:Z(15)= SGN (Z(9)):Z(
200:IF (H<-J/2 OR H>J/2)       -E*E)-V                        9)= ABS (Z(9)):Z(11)
THEN LET V=-1* ABS (           602:Z(6)=0:U=Z(4):B=.9*Q       = INT (Z(9)):Z(12)=Z
V)                             :D=I/2: GOSUB 750:Q=           (9)-Z(11)
202:I= SQR (V*V+R*R)           Z(9)                           830:Z(13)= INT (16*Z(12)
205:W=Q/K: IF ABS (I*          603:U=Z(2):B=1.07*Z(10):       +.5)
TAN (W))<=1 THEN 208           D=I/4: GOSUB 750:Z(1           835:IF Z(13)=0 THEN 900
206:Z(1)=ABS (I* TAN (W        0)=Z(9)                        840:IF Z(13)=16 THEN LET
)):R=R/Z(1):V=V/Z(1)           604:U=Z(3):B=1.07*H:           Z(11)=Z(11)+1:Z(13)=
:E=(G>0)-(G<=0):               GOSUB 750:H=Z(9)               0: GOTO 900
GOTO 380                       605:GOSUB 255: PRINT "TH       850:Z(14)=16
208:IF G<0 THEN LET E=-I       UMB DEPTH":Z(9)=Q:             860:IF Z(13)/2= INT (Z(1
* TAN (W)                      GOSUB 800                      3)/2) THEN LET Z(13)
209:IF G>=0 THEN LET E=1       606:PRINT "MID. FING. DE       =Z(13)/2:Z(14)=Z(14)
* TAN (W): GOTO 380            PTH":Z(9)=Z(10):               /2: GOTO 860
212:IF P>J/2 THEN LET V=       GOSUB 800                      867:IF Z(11)=0 THEN
-3: GOTO 214                   607:PRINT "RING FLING. DE      PRINT Z(15)*Z(13);"/
214:V=3: IF P>J/2 THEN         PTH":Z(9)=H: GOSUB 8           ";Z(14);"IN.":
LET O=(J-P)/K: GOTO            00: END                        RETURN
216                            690:Z(17)=0:Z(18)=0:Z(19       870:PRINT Z(15)*Z(11);"
216:O=P/K: IF H>0 THEN         )=0:O=0:W=0                    AND ";Z(13);"/":Z(14
LET R=V* TAN (O):              700:FOR P=1 TO LEN (A$)        );"IN."
GOTO 218                       701:IF MID$ (A$,P,1)=" "       880:RETURN
217:R=-V* TAN (O)              THEN LET Z(17)=P               900:PRINT Z(15)*Z(11);"
218:I= SQR (V*V+R*R):W=Q       702:IF MID$ (A$,P,1)="/"       IN."
/K:E=I* TAN (W)                THEN LET Z(18)=P               910:RETURN
224:IF E>1 THEN LET V=V/       704:NEXT P                     950:INPUT "GRIP WT.? ";A
E: GOTO 216                                                   $: GOSUB 690: RETURN
```

The operating system of the preferred embodiment as set out in TABLE VI has been prepared in a version of BASIC and is suitable for use on the SHARP brand pocket computer previously identified. It will be understood that the use of BASIC is an expedient and any variation of the operating system, for example, the use of another computer or operating system language still falls within the scope of the invention. Knowledge of BASIC and the following explanation of variables and operating system provides a complete description of the operating system. It will be understood that the variables not specifically defined in TABLE VII refer to standard procedures for designing operating systems in BASIC.

TABLE VII

| | |
|---|---|
| K = | Radius of a bowling ball; |
| J = | One-half of the circumference of a bowling ball; |
| S = | A vector directed from the center of the bowling ball toward one of the side hemispheres 206 or 208 of the bowling ball in which the magnitude of the vector represents a side weight component of the initial weight imbalance; |
| F = | A vector directed from the center of the bowling ball toward the finger or thumb hemisphere 210 or 212 of the bowling ball in which the magnitude of the vector represents a finger weight component of the initial weight imbalance; |
| T = | A vector directed from the center of the bowling ball toward the top or bottom hemisphere 214 or 216 of the bowing ball in which the magnitude of the vector represents a top weight of the initial weight imbalance/ |
| S, F and T = | Components of a resultant vector, the resultant vector representing an existing weight imbalance of a bowling ball; |
| R = | A vector parallel to S representing the magnitude of a final side weight component of a selected weight imbalance; |
| E = | A vector parallel to F representing the magnitude of a final finger weight component of a selected weight imbalance; |
| V = | A vector parallel to T representing the magnitude of a final top weight component of a selected weight imbalance; |
| R, E and V = | Components of a resultant vector, the resultant vector representing a desired weight imbalance of a bowling ball; |
| I = | The magnitude of an imbalance vector corresponding to the difference of two resultant vectors representing an amount by which the bowling ball is in imbalance, the existing and desired weight differences may be considered as vector components of the two resultant vectors wherein one resultant vector represents the resultant of existing weight differences and another resultant vector representing the resultant of the desired weight differences, the magnitude of vector I represents the total weight imbalance change that is sought by the bowler or the driller; |
| X, Y and Z = | Magnitudes of components of the vector I; |
| L = | Horizontal distance from center of palm to the location at which a hole that would have to be drilled to provide the desired imbalance in the bowling ball; |
| M = | Vertical distance from center of palm to the location at which a hole that would have to be drilled to provide the desired imbalance in the bowling ball; |
| H = | Horizontal measurement from center of palm to axis of roll converted to a decimal from a fraction; |
| G = | Vertical measurement from center of palm to axis of roll converted to a decimal from a fraction; |
| O, W = | A central angle defined by the known relationship, Distance = (Radius) (Central Angle); |
| Z(2)/2 = | Radius of middle finger; |
| Z(3)/2 = | Radius of ring finger; |
| Z(4)/2 = | Radius of thumb; |
| Z(0) = | Span; |
| Z(10) = | Weight of grip used in middle finger grip hole; |
| H = | Weight of grip used in ring finger grip |

TABLE VII-continued

| | |
|---|---|
| | hole, H is used to represent two different variables and its meaning will be understood from the context of the operating system; |
| Q = | Weight of grip used in thumb grip hole, Q is used to represent two different variables and its meaning will be understood from the context of the operating system; and |
| B = | Relative weight change resulting from drilling a grip hole which is partially refilled by inserting a finger grip or thumb grip into the drilled hole |

It will be understood that center of palm, as used in TABLEs VII and VIII, may refer either to the MRP, TRP or ARP depending upon the application.

It will be understood that a weight imbalance created between a pair of hemispheres of a bowling ball, when a hole is drilled in one of the hemispheres, is not necessarily equal to the weight of the material removed from the bowling ball due to the hole. Once this is understood it is possible to quantify at least two important features of the present invention. First, determining where to drill a hole and to what depth so as to achieve a desired weight imbalance between two bowling ball hemispheres. Second, determining the location of thumb and finger grip holes, or a balance hole, so as to achieve a desired weight imbalance in a bowling ball. Once the second feature is realized it is then possible, as accomplished by the present invention, to locate where it would be possible to drill a single hole of appropriate diameter and depth so as to create the desired weight imbalance and to locate thumb and finger grip holes such that the thumb grip hole accounts for one-half ($\frac{1}{2}$) of the desired weight imbalance and may be located on a great circle through the second and third intersection points and each finger grip hole (the ring and middle finger) accounts for one-quarter ($\frac{1}{4}$) of the desired weight imbalance. These theories and features are represented in a preferred embodiment of the operating system of the present invention illustrated in TABLE VI and further described below.

The operating system may be separated into different areas for convenience of description and understanding.

In Lines 5 and 6 certain variables are initialized. Lines 12 through 36 provides for existing and desired weight input into the operating system.

The Lines 38 and 40 establish important vector relationships between the existing weight imbalance and the desired weight imbalance while Line 42 initializes the variables representing the value of the first coordinate and the second coordinate.

Lines 54 through 58 are the first of numerous conditional command statements used throughout the operating system in order to first establish a relationship between existing weight imbalances and desired weight imbalances and then proceed to subsequent operative statements of the operating system. Line 59 represents an appropriate determining statement for the variable M when the conditional command statements, that if true, command the operating system to follow a particular path. This is the general purpose of any conditional command statement. Accordingly, Line 64 represents an appropriate determining statement for the variable M under conditions of existing weight imbalance and desired weight imbalance based upon conditions determined by the logically proceeding conditional command statements.

Line 66 is another conditional command statement and Line 68 represents an appropriate determining statement for variable L under conditions of existing weight imbalance and desired weight imbalance based upon conditions determined by the logically proceeding conditional command statements.

Lines 72 through 78 are the next group of conditional command statements and Line 80 represents an appropriate determining statement for the variables L and M under conditions of existing weight imbalance and desired weight imbalance based upon conditions determined by the logically proceeding conditional command statements.

The next lines, Lines 84 through 92, represent the next group of command and conditional command statements in the logical progression of the illustrated embodiment of the operating systems, while Line 94 represents the next appropriate determining statement for the variable L.

In the following Lines 96 through 184, similarly, Lines 104, 108, 114, 120, 122, 126, 138, 142, 158, 170 represent the remaining conditional command statements relating to the relationship between the measured or existing weight imbalance and the desired weight imbalance; Lines 98, 102, 106, 117, 118, 128, 140, 146, 148, 154, 156, 166, 168, 172, 176, 178, 184 represent the appropriate determining statements for the variables L and M and Lines 110, 124, 144, 152, 160 represent standard "GO TO" statements, the use and purpose of which will be understood from the context of the operating system.

The next lines, Lines 188 through 252 represent the determining statements for the final relative side weight, relative finger weight and relative top weight and the necesary commands to proceed to the output portion of the operating system.

In Lines 254, and 255 the desired output, for example, grip holes or a balance hole is determined, identifying the corresponding portions of the operating system that will be required to make the requested determinations.

Additional output is represented by lines 256 through 382.

The use of the operating system to determine final weight imbalances is reflected in Lines 386 through 388.

The portions of the operating system corresponding to the condition of a bowling ball, for example, new or drilled, are selected in response to the inquiries of lines 400 through 406.

Initial values of span, finger and thumb size and ball weight are input to the operating system and corresponding sizes are determined at Lines 407 through 415.

Lines 499 through 604 represent steps in the process of determining values for the variables M, I and the diameter and depth of the hole or holes required to satisfy the desired weight imbalance conditions.

Output of thumb, middle finger and ring finger depth is represented by lines 605 through 607.

Lines 690 through 711 illustrate a subroutine for converting inches and fractions of an inch to a single decimal number.

Lines 750 through 760 represent a subroutine to determine hole depth required to accomplish a desired weight imbalance.

Lines 800 through 910 illustrate a subroutine for converting a decimal number into a whole number and a fraction.

Finally, Line 950 relates to a subroutine for inputting grip weights.

Referring again to TABLE VI, the source code for the operating system of the illustrated embodiment will now be described in somewhat greater detail in TABLE VIII. It will be understood that while the operating system disclosed in TABLE VI corresponds to a preferred embodiment of the present invention other variations are possible for different hardware, i.e. computers, and in different programming languages, not only the presently used version of BASIC as illustrated herein. Some of the lines of the source code from TABLE VI will not require further description since they will be readily understood and will not be represented in TABLE VIII.

TABLE VIII

| LINE | DESCRIPTION |
|---|---|
| 5 | The dimension of "Z" is established to accomodate all of the necessary values to be used; the use of radians is established; the values of "K" and "J" are set. |
| 6 | Z(6) is initially set equal to 1 and the operating system moves to Line 400 of the source code for the next step. |
| 12 | The user is instructed to input an existing side weight and the existing side weight is labelled "S". |
| 14 | The user is instructed to input an existing finger weight and the existing finger weight is labelled "F". |
| 16 | The user is instructed to input an existing top weight and the existing top weight is labelled "T". |
| 18 | The user chooses whether the user will select a final weight difference for the bowling ball by inputting "Y", or whether the operating system will determine the final weight difference for the bowling ball by inputting "C". |
| 24 | A "GO TO" statement in case neither "Y" nor "C" is input at Line 18. |
| 32 | If the statement at Line 20 is true, then the user is instructed to input a desired side weight and the desired side weight is labelled "R". |
| 34 | The user is instructed to input a desired finger weight and the desired finger weight is labelled "E". |
| 36 | The user is instructed to input a desired top weight and the desired top weight is labelled "V". |
| 38 | See TABLE VII, definition of "I". |
| 40 | See TABLE VII, definition of "X", "Y" and "Z". |
| 42 | To provide a bowling ball with a desired weight imbalance it is usually necessary to drill at least one hole in the bowling ball, from TABLE VII "L" and "M" represent the horizontal and vertical distance, respectively, from whatever reference point is being used, e.g. MRP, TRP, ARP or center-of-palm. |
| 54 | An "IF-THEN" statement which is true if the existing side weight difference (or relative side weight) does not need to be changed in which case "L" remains at its current value of zero and Line 72 is the next statement. |
| 56 | An "IF-THEN" statement which is true if the existing finger weight difference (or relative finger weight) does not need to be changed in which case "M" remains at its current value of zero and Line 86 is the next statement. |
| 58 | An "IF-THEN" statement which is true if the existing top weight difference (or relative top weight) does not need to be changed in which case "L" corresponds to ¼ of the circumference of the bowling ball and the hole will be located on a great circle dividing the bowling ball into the top half and the bottom half and Line 96 is the next statement. |
| 59 | The statements at Lines 54, 56 and 58 were all false if this statement is reached and that neither "X" nor "Y" nor "Z" equals zero in which case the vertical distance "M" equals the right side of the expression in this statement. |
| 60 | An "IF-THEN" statement which is true if the existing side weight difference (or relative side weight) is greater than the desired relative side weight in which case the balance hole must be drilled in the positive side of the bowling ball and Line 104 becomes the next statement. |
| 62 | An "IF-THEN" statement which is true if the existing finger weight difference (or relative finger weight) is greater than the desired relative finger weight in which case the balance hole must be drilled in the positive finger half of the bowling ball and Line 114 becomes the next statement. |
| 64 | The statements at Lines 60 and 62 were both false if this statement is reached, compared to the statement at Line 59, the statement at Line 64 is the same but in the opposite direction. |
| 66 | An "IF-THEN" statement which is true if the existing relative top weight is greater than the desired relative top weight, if the statement at Line 66 is true then the vertical distance to the balance hole is in a positive direction from the corresponding reference point. Line 118 becomes the next statement if the Line 66 statement is true. |
| 68 | The statements on Lines 54 through 62 were false in order to reach the statement on Line 68, it must be true that "S" is less than "R" indicating that more side-weight is required to provide the desired or selected weight imbalance for a bowling ball, the horizontal measurement to the balance hole will be to the left of the corresponding reference point on the bowling ball or in the negative direction; a "GO TO" statement indicates that the next statement is located at Line 254. |
| 72 | An "IF-THEN" statement which is true if the existing relative finger weight is correct in which case the vertical distance from the corresponding reference point to the center of palm will be zero and Line 210 contains the next statement. |
| 76 | An "IF-THEN" statement which is true if the existing relative top weight is correct and does not need to be changed in which case "L" corresponds to ¼ of the circumference of a bowling ball and the hole will be located on a great circle dividing the bowling ball into the top half and the bottom half and the next statement is located at Line 126. |
| 78 | An "IF-THEN" statement which is true if the existing relative top weight exceeds the desired relative top weight resulting in the balance hole being located in the hemisphere of the bowling ball containing the gripping holes and the next statement is located at line 170. |
| 80 | If this statement is reached then from the statements at Lines 76 and 78 it is known that "T" may be less than "V" and more top weight is required, the horizontal distance from the corresponding reference point to the balance hole becomes ½ of the circumference and if the existing relative finger weight is too great then the distance from the corresponding reference point will have a vertical component, in view of the "GO TO" statement Line 254 becomes the next statement when the "IF-THEN" statement is true. |
| 84 | A "GO TO" statement reached if the statement at Line 80 is false, Line 172 becomes the next statement where the vertical component "M" will be assigned a negative value. |
| 86 | An "IF-THEN" statement which is true if the existing relative top weight is equal to the desired relative top weight, the statement at Line 56 was true in order to reach this statement, if this statement is true, then the only weight imbalance correction available is relative side weight and the measure of horizontal distance will be set equal to a positive or a negative ¼ of the circumference |

TABLE VIII-continued

| LINE | DESCRIPTION |
|---|---|
| | of the bowling ball relative to the corresponding reference point, Line 138 becomes the next statement. |
| 90 | An "IF-THEN" statement which is true if the existing relative top weight exceeds the desired relative top weight and Line 142 becomes the next statement. |
| 92 | An "IF-THEN" statement which is true if the existing relative side weight is greater than the desired relative side weight and Line 146 becomes the next statement. |
| 94 | The horizontal measurement "L" is determined by the statement at Line 254 and is measured from a point opposite the corresponding reference point, the measurement is determined by a subtended arc that is the arctangent of the ratio of "X" and "Y", a "GO TO" statement indicates that Line 254, the next statement refers to the output portion of operating system. |
| 96 | An "IF-THEN" statement which is true if the existing relative side weight is greater than the desired relative side and Line 148 becomes the next statement. |
| 98 | This statement may be reached when the statement at Line 58 is true and the statements at Lines 54, 56 and 96 are false, the existing top weight is acceptable and the horizontal measurement is equal to ¼ of the bowling ball circumference in the negative direction from the corresponding reference point and the balance hole is located on the great circle dividing the top half from the bottom half, additionally, should the existing relative finger weight be greater than the desired relative finger weight then the vertical dimension will be positive, otherwise it will be negative. |
| 102 | A statement definine "M" when additional relative finger weight is required, "M" becomes negative as indicated by the statement at Line 98, a "GO TO" statement indicates that Line 254 contains the next statement. |
| 104 | An "IF-THEN" statement which is true if the existing relative finger weight is greater than desired in which case the vertical distance to the balance hole will be positive and Line 156 contains the next statement. |
| 106 | If the statement at Line 104 was false, then this statement will be reached in which case more finger weight is required to satisfy the desired relative weights, the additional finger weight is obtained by making "M" negative toward the negative finger (or thumb) hemisphere, it will be noted that "M" in the statements in Lines 106 and 59 are determined similarly. |
| 108 | An "IF-THEN" statement which is true if the existing relative top weight is greater than the desired relative top weight in which case Line 178 contains the next statement. |
| 110 | A "GO TO" statement reached if the statement at Line 108 is false, Line 146 becomes the next statement. |
| 114 | An "IF-THEN" statement which is true if the existing relative top weight is greater than the desired relative top weight in which case Line 118 contains the next statement. |
| 117 | The vertical distance from a corresponding reference point to the balance hole is determined, a "GO TO" statement indicates that Line 94 is the next statement. |
| 118 | This statement determines the horizontal distance from the corresponding reference point to the balance hole, the arctangent of the ratio of "X" to "Y" represents a measurement of an angle between a vector represented by "X" and a vector represented by "Y", using the known expression for distance (see TABLE VII) the horizontal distance from the corresponding reference point to the balance hole may be determined, a "GO TO" statement indicates that Line 254 contains the next statement. |
| 120 | An "IF-THEN" statement which is true if the existing relative top weight is correct in which case the horizontal distance between a corresponding reference point and the balance hole will be ¼ of the circumference of the bowling ball and Line 252 contains the next statement. |
| 122 | An "IF-THEN" statement which is true if the existing relative top weight is less than the desired relative top weight, indicating that the balance hole will be in a hemisphere of the bowling ball opposite a hemisphere containing the grip holes and the next statement is contained in Line 166. |
| 124 | A "GO TO" statement reached if the statement at Line 122 is false indicating that the horizontal and vertical distances between the corresponding reference point and the balance hole will remain as previously defined and that the next statement is contained on Line 254. |
| 126 | "An "IF-THEN" statement which is true if the existing relative finger weight is less than the desired relative finger weight in which case the balance hole must be drilled in a negative vertical direction or towards the thumb grip hole and Line 168 contains the next statement. |
| 128 | This statement is reached if the existing relative finger weight is greater than the desired relative finger weight in which case the vertical distance to the balance hole will be ¼ of the circumference of the bowling ball, a "GO TO" statement indicates that Line 254 contains the next statement. |
| 138 | An "IF-THEN" statement which is true if the existing relative side weight is greater than the desired relative side weight in which case Line 176 contains the next staement. |
| 140 | This statement is reached if the existing relative side weight is less than the desired relative side weight in which case the horizontal distance to a balance hole from a corresponding reference point will be negative indicating movement of the balance hole to the left with respect to the corresponding reference point, a "GO TO" statement indicates that Line 254 contains the next statement. |
| 142 | An "IF-THEN" statement which is true if the existing relative side weight is greater than the desired relative side weight in which case line 178 contains the next statement. |
| 144 | A "GO TO" statement indicating that the previous statement was false and that the next statement is contained in Line 118. |
| 146 | This statement contains an expression for "L" indicating that a balance hole must be drilled in a hemisphere of the bowling ball opposite the hemisphere of the bowling ball that contains the gripping holes and the "GO TO" statement indicates that Line 254 contains the next statement. |
| 148 | This statement contains an expression for "L" setting the horizontal distance between the balance hole and a corresponding reference point to ¼ of the circumference of the bowling ball and an "IF-THEN" statement which is true if the existing relative finger weight is greater than the desired relative finger weight in which case the next statement is contained in Line 154. |
| 152 | A "GO TO" statement indicating that the statement in Line 148 was false resulting in Line 102 containing the next statement. |
| 154 | A statement containing an expression for "M" determining the vertical distance to a balance hole from a corresponding reference point and a "GO TO" statement indicating that Line 254 contains the next statement. |
| 156 | This statement contains an expression for "M" in which the vertical distance to the balance hole from a corresponding reference point is determined. |
| 158 | An "IF-THEN" statement which is true if the existing relative top weight is greater than |

TABLE VIII-continued

| LINE | DESCRIPTION |
|------|-------------|
|  | desired relative top weight in which case Line 178 contains the next statement. |
| 160 | A "GO TO" statement indicating that the statement at Line 158 was false and further indicating the Line 146 contains the next statement. |
| 166 | A statement containing an expression for "L" indicating that the horizontal distance between the balance hole and the corresponding reference point will be ¼ of the circumference of the bowling ball and that the balance hole will be located on an arc dividing the bowling ball into a first side and a second side in which case the relative side weight will not change, a "GO TO" statement indicates that Line 254 contains the next statement. |
| 168 | This statement contains an expression for "M" indicating that the vertical distance between a balance hole and a corresponding reference point will be ¼ of the circumference of the bowling ball and in the negative direction, a "GO TO" statement indicates that Line 254 contains the next statement. |
| 170 | An "IF-THEN" statement which is true if the existing relative finger weight is greater than the desired relative finger weight in which case the next statement is contained in Line 184. |
| 172 | This statement contains an expression for "M" indicating that the vertical distance between the balance hole and the corresponding reference point will be in the negative direction since the existing relative finger weight is less than the desired relative finger weight, a "GO TO" statement indicates that Line 254 contains the next statement. |
| 176 | This statement contains an expression for "L" indicating that the existing relative top weight is correct such that the horizontal distance between the balance hole and the corresponding reference point must be determined such that the relative top weight is not affected and that the horizontal distance is ¼ of the circumference of the bowling ball in a positive direction, a "GO TO" statement indicates that line 254 contains the next statement. |
| 178 | This statement contains an expression for "L" determining the horizontal distance between the balance hole and the corresponding reference point, a "GO TO" statement indicates that line 254 contains the next statement. |
| 184 | This statement determines "M", the vertical distance between a balance hole and a corresponding reference point, a "GO TO" statement indicates that Line 254 contains the next statement. |
| 188 | A statement prompting the user to input the "horizontal measurement to the axis of roll from the corresponding reference point to the point of intersection of the axis of roll on the ball's surface" a distance which as previously described may be obtained by using the ball cradle, the measurement "A$" is input in inches and fractions of an inch, a subroutine that starts on Line 690 is used to convert the horizontal measurement into a decimal number which is then defined as "Z(16)" which is then stored as the value of "H". |
| 190 | This statement is similar to the statement on Line 188 except that it refers to the vertical measurement between the axis of roll and the corresponding reference point, again the subroutine starting at Line 690 is used to convert the inch and fraction of an inch as input to a decimal number which is then stored as the value of "G". |
| 192 | A statement establishing the values of the variables "P" and "Q". |
| 193 | This statement determines whether the relative top weight exceeds the 3.0 ounce limit established by the American Bowling Congress, it is an "IF-THEN" statement which if true indicates that the relative top weight is greater than allowed and that the next statement therefore is located at Line 212, "P" is defined in the statement at Line 192. |
| 194 | An "IF-THEN" statement determining the value of "R" relative to the sign of "H" where "H" was defined as a horizontal measurement from a corresponding reference point to the axis of roll, "R" represents the relative side weight of the balanced bowling ball if the axis of roll is located in the negative direction with respect to the corresponding reference point in which case the value of "R" is considered to be negative and the maximum allowed relative side weight is one ounce in accordance with American Bowling Congress regulations. |
| 195 | An "IF-THEN" statement which if true sets the value of the variable "R" to a positive one resulting from the axis of roll being in the positive direction with respect to the corresponding reference point and the final relative side weight is equal to 1, the maximum magnitude allowed under present American Bowling Congress regulations. |
| 196 | This statement initially establishes the value of the angle "O" unless the following "IF-THEN" statement is true in which case the value of "O" is re-established in which case the axis of roll is in a hemisphere of the bowling ball opposite the hemisphere of the bowling ball containing the gripping holes, the angle "O" is determined using the formula for distance from TABLE VII. |
| 198 | This statement determines "V" as the final relative top weight of the balanced bowling ball based upon the values of "R" and the angle "O" determined in the preceding statements Lines 193, 194, 195 and 196. |
| 200 | This statement contains an "IF-THEN" statement that establishes the value of "V" depending upon whether the axis of roll intersects the bowling ball surface at a point that lies in the bottom hemisphere with respect to gripping holes in which case the final relative top weight will have a negative value. |
| 202 | The expression for "I" is determined by using the Pythagorean Theorem to determine the resultant of two components that represent relative side and relative top weight in a balanced bowling ball, the magnitude of "I" is equivalent to the leg of a right triangle that is used to calculate the relative finger weight of the balanced ball, the central angle that will be used comes from the measure of vertical distance from the corresponding reference point to an axis of roll. |
| 205 | This statement defines "W" and contains an "IF-THEN" statement that reflects the maximum relative finger weight of 1.0 ounce as determined by existing American Bowling Congress regulations such that the next statement is Line 208 if the relative finger weight for the bowling ball being balanced is less than or equal to 1.0 ounce. |
| 206 | The statement is reached if the statement in Line 205 is false indicating that the assumption that the side weight is equal to 1 ounce or −1 ounce leads to a finger weight greater than 1 ounce or less the −1 ounce which is contary to current American Bowling Congress regulations, the values for "R" and "V" are scaled down by the factor "Z(1)" defined with respect to "W", the value of "E" is determined as either a negative or a positive value depending on whether the vertical distance from the axis of roll to the corresponding reference point is in the negative or positive direction, a "GO TO" statement indicates that Line 380 contains the next statement. |
| 208 | An "IF-THEN" statement determining the value of "E" based upon the sign of "G" in which case if true indicates that the vertical distance to the axis of roll from a corresponding reference point is positive and therefore the relative finger weight will be positive, a "GO TO" statement indicates that the next statement is at Line 380 |

TABLE VIII-continued

| LINE | DESCRIPTION |
|---|---|
| | which includes the output of the results of the determination with respect to the finger weight. |
| 209 | An "IF-THEN" statement that determines the value of "E" when "G" is greater than or equal to zero indicating that the vertical distance of the axis of roll from the corresponding reference point is positive in which case the relative finger weight will be positive, a "GO TO" statement indicates that the next statement is at Line 380 which includes the output of the results of these determinations for the relative finger weight. |
| 212 | This statement initially sets the value of "V" unless the following "IF-THEN" statement is true in which case the value of "V" is redefined, the initial value of the relative top weight is set equal to 3 and then redefined as −3 if the horizontal distance from the corresponding reference point to the balance hole is greater than ¼ the circumference of the ball, redefining "V" as −3 redefines the balance hole as being located on the bottom half of the bowling ball. |
| 214 | This statement initially defines the value of the angle "O" and then contains an "IF-THEN" statement that redefines the value of the angle "O" if the statement is true. |
| 216 | In this statement the value of "R" is initially determined such that the desired relative side weight will have a magnitude that will form a right triangle (remembering that "R" and "V" are vectors and the angle "O" is the measure of the angle opposite "R" and the value of "R" is defined to be negative unless the "IF-THEN" statement is false in which case the horizontal distance to the axis of roll from the corresponding reference point will be positive and "R" will be redefined to be positive as well. |
| 218 | This statement first determines the value of "I" as the magnitude of the resultant of two perpendicular vectors pointing respectively to the top or bottom portions of the bowling ball and to either the first side or second side of the bowling ball, then "W" is defined by using the vertical distance to the axis of roll from the corresponding reference point namely "Q" and the radius of the bowling ball, finally, "E" the desired relative finger weight is determined as the length of the leg of a right triangle defined by the corresponding vectors opposite the angle "W" the other leg of which is perpendicular to "E" and which has a magnitude equal to "I". |
| 224 | An "IF-THEN" statement in which the desired value of "E" as determined in the statement at Line 218 is checked to see that it falls within the approved ranges according to the American Bowling Congress regulations and if it does not or if the statement is false then "V" is redefined by dividing by the value of "E", a "GO TO" statement indicates that if the statement Line 224 is true then the next statement is at Line 216 at which time the corresponding variables will be determined using the new value of "V". |
| 226 | An "IF-THEN" statement which is true if the vertical distance from the corresponding reference point to the axis of roll is negative in which case the relative finger weight will be considered negative and the sign of "E" will be changed but not the magnitude. |
| 228 | A "GO TO" statement indicating that the preceding statements are true in which case the next statement is at Line 380 and the operating system proceeds with the output portion showing the results of the determinations in the preceding statements. |
| 252 | This statement is reached if the desired relative side weight, relative finger weight and relative top weight are equal to the existing relative side weight, relative finger weight and relative top weight, respectively, in which case a balance hole is not necessary. |
| 254 | This statement allows some of the previous statements to be used for more than one application, for example, when the product equals one that indicates that a new ball is being drilled and that the output portion that indicates the location of the balance hole may be omitted. |
| 255 | An "IF-THEN" statement that if true indicates that the next statement is located at Line 500 and that a new bowling ball is being drilled. |
| 256 | An output statement for the horizontal and vertical distances to a balance hole from a corresponding reference point in which "Z(9)" is used by a subroutine that starts at Line 800 which converts a decimal value into inches and fractions of an inch. |
| 257 | This is a statement relating the drilling of a new bowling ball and the balancing of a previously drilled bowling ball incorporating output information regarding finger and thumb holes in the case of a new bowling ball being drilled and a balance hole in the case of a previously drilled bowling ball be balanced, when a previously drilled bowling ball is to be balanced a single balance hole is drilled "L" inches horizontally displaced and "M" inches vertically displaced from the corresponding reference point and the relative weight difference created by the balance hole is equal in magnitude to "I", but when a new bowling ball is being drilled three holes are drilled to create the same effect as one balance hole in which case each finger hole will account for ¼ of the relative weight difference required and the thumb grip hole account for ½ the relative weight difference required |
| 258 | A print statement indicating the amount of weight in ounces to be removed and the user will remove enough weight to make this difference between the side with the balance hole and the side opposite the balance hole and the actual amount of weight that must be removed will be found in a TABLE by using the output provided by this statement. |
| 380 | A print statement that prints the ending side weight which corresponds to the maximum side weight that can be used to balance the bowling ball, the expression in the statement rounds off the output to the nearest .01 ounce. |
| 381 | A print statement including output indicating to the user the correct finger weight to result in a balanced bowling ball assuming that the relative side weight is at a maximum value, the expression included in Line 381 rounds off the output to the nearest .01 ounce. |
| 382 | A print statement including the correct relative top weight resulting in a balanced bowling ball, the expression for "INT" rounds off the output to the nearest .01 ounce. |
| 386 | An input statement wherein the user establishes the percentage of the maximum allowable weight according to the American Bowling Congress regulations and the percentage is represented by the variable "Z(5)" and an "IF-THEN" statement that if true indicates that a value of more than 100% was input in which case the input query is again made in order to allow the user to input the correct percentage desired, if less than the 100% maximum effect of the relative weight differences is desired the user may choose any percentage between −100% and +100%, inclusively, and the operating system then redetermines the values of the variables "R", "E" and "V" by multiplying by the input percentage. |
| 387 | An "IF-THEN" statement that changes the input statement at Line 386 to decimal form. |
| 388 | This statement scales the magnitude of the variables "V", "R" and "E" to the requested percentage of the maximum such that the resultant of these three perpendicular vectors will change in magnitude but not in direction. |
| 400 | This statement initially defines the variable "Z(7)" and includes an input statement in which |

TABLE VIII-continued

| LINE | DESCRIPTION |
|---|---|
| | the user indicates whether the bowling ball is a new bowling ball or a previously drilled bowling ball. |
| 402 | An "IF-THEN" statement which if true indicates that the bowling ball already has gripping holes drilled in it and possibly needs the location of a balance hole determined and the next statement is located at Line 12. |
| 404 | An "IF-THEN" statement that redefines the variable "Z(7)" if the input statement at Line 400 is "N" indicating that relative weights are to be determined for a new bowling ball and a "GO TO" statement indicating that Line 12 contains the next statement. |
| 406 | A "GO TO" statement indicating that the next statement is Line 400 if neither "D" nor "N" was selected in response to the statements at Lines 400 and 402, such that the question regarding a new or a drilled bowling ball is asked again. |
| 407 | An input statement for inputting the span of the bowler's hand which is then set equal to "A$" and is then converted to a decimal at subroutine 690 in which the span is the average distance between the thumb grip hole and the two finger grip holes and the span will be used to determine the depths of the thumb and finger grip holes since the thumb and finger grip holes will be offset from a point defined by "L" and "M" by an amount that is defined by the span and it will be necessary to accomodate this offset when determining the effect of drilling a hole in the bowling ball, reference is made to the statement on Line 750 wherein this effect is taken into account by using a value for "COS(Z(0))" as a factor in determining the amount of weight to be removed to create the desired state of imbalance in the bowling ball. |
| 408 | This statement defines the variable "Z(10)" and the input of the middle finger size is defined as variable "A$" and subroutine 690 is used to convert the input to a decimal and grip weights if grips are used will also be input and converted to a decimal by subroutine 690. |
| 409 | The statement receives the input of the finger size and weight of the finger grip if any and converts these sizes and weights to decimals, it will be noted that the variable "H" is used again only to conserve the memory of the pocket computer used in a preferred embodiment |
| 412 | This statement accepts the input of the thumb diameter and grip weight, if any, and converts both to a decimal number. |
| 413 | This is an input statement for the bowling ball weight in pounds which is then set equal to "Z(8)". |
| 414 | This statement is necessary in view of the fact that a bowling ball driller usually measures the span of tne bowler's hands between the insides of the gripping holes, however, since the weight is determined to be equivalent to have been taken from the center of each hole it is necessary to determine the average distance from the thumb grip hole to the center of each finger grip hole and the expression in this statement is the average of the two distances. |
| 415 | This statement results in false statements at Lines 254 and 255 thereby signaling to the operating system that a new bowling ball is being drilled. |
| 499 | This statement contains expressions that determine the location of the three gripping holes in order to achieve a desired bowling ball imbalance. |
| 500 | This statement contains a number of expressions used to determine the location of finger and thumb grip holes in order to obtain the desired bowling ball imbalance. |
| 602 | This statement contains an expression used to determine the depth of the thumb grip hole with or without thumb grips such that thumb grip hole depth is determined in order to produce ⅓ of the desired weight imbalance required for a balanced bowling ball, understanding that each finger grip hole will generate ⅓ of the weight difference, the variable "U" is used by the subroutine starting at Line 750 to determine hole depth, "U" is set equal to Z(4) in order to determine thumbhole depth since Z(4) represents thumbhole diameter from Line 412, the value of "Q" was determined in Line 412 unless no grips are used and "Q" equals zero, "B" is set equal to (.9)(Q) where "B" represents the amount of additional weight that must be removed to compensate for insertion of the grip and the .9 factor is preferable because thumb grips are approximately 2.625 inches long, D is defined as I/2 in order that the thumbhole depth may be determined such that the thumbhole will generate ⅓ of the desired weight difference determined for a desired imbalance or balance for a bowling ball, Lines 603 and 604 define D as I/4 since each finger hole provides ⅓ of the desired weight difference, Q then equals Z(9) which is the depth of the thumbhole. |
| 603 | This statement is similar to the statement at Line 602 and establishes the variables needed by subroutine 750 to determine middle finger grip hole depth with or without the use of grips in which the middle finger grip hole will account for ⅓ of the total desired or required change in weight difference the variable "U" is again used to conserve memory and is set equal to Z(2) in order to determine middle finger hole depth since Z(2) represents middle finger hole diameter from Line 408, the value of Z(10) was determined in Line 408 unless no grips are used and Z(10) equals zero, "B" is set equal to (1.07)(Z(10)) where "B" represents the amount of additional weight that must be removed to compensate for insertion of the grip and the 1.07 factor is preferable because finger grips are approximately 1.5 inches long, again as in Line 602, D is defined as I/4 and upon completion of a hole depth determination in subroutine 750 Z(10) is set equal to hole depth, Z(9). |
| 604 | This statement is similar to the statements in Line 602 and 603 except it pertains to the determination of the depth of the ring finger grip hole. |
| 605 | This statement initially refers to a subroutine and begins with the statement at Line 255 for determining and printing the thumb grip hole depth and uses the subroutine starting at Line 800 for converting a decimal number into a whole number and a fraction for the desired output, the subroutine determines whether it is possible to remove enough weight to achieve the desired bowling ball imbalance and if it is not possible will redetermine for all the gripping holes based on a new value of the variable "I" which will be decreased by the statement in Line 760, repeating the determination until "I" is so small that the desired weight difference can be created with the gripping holes, it is indicated at Line 255 whether it is possible to remove enough weight from the bowling ball to achieve the desired balance (or imbalance) if it is not possible then Z(6) will equal 2 in the statement in Line 760, this results in a decreased value of "I" at Line 760 and redeterminations of all the gripping holes will be made based on the new value of "I", the redetermination will continue until the value of "I" is sufficiently decreased that a desired weight difference may be created with the gripping holes and whenever a new value for "I" must be determined the weight removed from the bowling ball will not equal the original amount of weight required to balance the bowling ball and after drilling the gripping holes the bowling ball will have a relative top weight in excess of that originally indicated, determinations of horizontal and vertical distances from a |

TABLE VIII-continued

| LINE | DESCRIPTION |
|---|---|
|  | corresponding reference point use the same statements and logic as that for balancing a previously drilled bowling ball since the logic in both situations requires the location of the source of the bowling ball imbalance and determination of the magnitude of the imbalance, however, even if three (3) grip holes are required instead of a single balance hole, the logic remains substantially similar for balance holes and grip holes and horizontal and vertical distances are determined from a corresponding reference point to a location for a balance hole but instead the location of the balance hole establishes a center-of-palm and one-half the weight is removed by a thumbhole and one-half the weight is removed by a pair of finger grip holes, ¼ of the weight for each finger hole, it will be understood that relative side weight should be correct since the grip holes are symmetric with respect to an associated arc that divides the bowling ball into the first side and the second side and it becomes apparent from the foregoing that relative top weight will be the least accurate relative weight generally because bowling balls can be manufactured with a wide range of weight block sizes and weights and because finger and thumb sizes may also vary greatly, therefore, it is possible that in some situations more weight will have to be removed to balance or provide a desired imbalance for a bowling ball than can easily be provided with generally accepted gripping hole drill bit sizes and it then becomes necessary to reduce the total amount of weight removed and proportion the reduction in weight removed evenly between thumb and finger grip holes, it will be further understood that regardless of the weight removed the relative finger weight and relative side weight will be as originally determined and if the total amount of weight differences originally determined has to be reduced then only the relative top weight is affected, in most instances a bowling ball may be drilled as determined by the operating system and then balanced with a balance hole in which case the balance hole is located on the surface of the bowling ball where a hole may be drilled to decrease relative top weight and not change relative side weight or relative finger weight. |
| 606 | This statement is similar to the statement in Line 605, with particular reference to the foregoing description, and pertains to determining and printing a grip hole depth for a bowler's middle finger. |
| 607 | This statement is similar to the statement in Lines 605 and 606 and pertains to determining and printing a grip hole depth for a bowler's ring finger and subsequently ending operation of the operating system. |
| 690 | The statements contained in Lines 690 through 711 convert inches and fractions of an inch to a single decimal number. |
| 750 | These statements have been previously discussed, if the value of Z(9) is less than zero then it will not be possible to remove sufficient weight from the bowling ball to provide the desired or selected weight imbalance using drill bits required for the indicated thumb and finger grip holes, therefore, the value or magnitude of "I" must be reduced and the new value or magnitude of "I" used to redo the previous determinations |
| 752 | This statement in the subroutine determines Z(9) if Z(9) was greater than or equal to zero at Line 750, the subroutine ends and the operating system continues at either Line 602, 603 or 604, respectively. |
| 760 | As indicated at Line 750 it may happen that not enough weight can be removed with the respective drill bits, the statement at Line 760 indicates a signal to the user and a reduction of the magnitude of "I" by a factor of .9 and a return to previous statements to redetermine all of the hole depths. |
| 800 | The statements contained in Lines 800 through 920 convert decimal numbers to inches and fractions of an inch. |
| 950 | This statement provides for the input of grip weights, and the subroutine at Line 690 indicates that grip weight may be input as a fraction. |

From the foregoing description and examples those skilled in the art will appreciate that all of the aspects of the present invention are realized. A bowling ball weight locator method and apparatus for implementing the method and performing the steps of the method is provided. The present invention includes means for locating an accurate reference point for use by a driller or a manufacturer, means for locating finger and thumb grip holes for a particular bowler's grip or a blanace hole on either an undrilled bowling ball or a previously drilled bowling ball so as to provide a desired bowling ball imbalance or a concentration of the weight as axis weight along the axis of roll and apparatus for implementing the method. The method and apparatus of the present invention provide for accurately determining a desired imbalance of a bowling ball without trial and error but yet simple and straightforward enough to be used by either bowling ball manufacturers or owners and operators of bowling ball drilled equipment. The present method and the described apparatus combine to provide quick, relatively error-free results. Incoporated into the present invention are the American Bowling Congress regulations regarding ranges of allowed bowling ball imbalance. The technique and apparatus of the present invention are easy to learn even by a relatively unskilled person. The present invention utilizes a series of repetive steps for various aspects thereby minimizing the number of steps that must be learned and apparatus to become familiar with in order to practise the present invention. It will be understood from the foregoing description of the present invention that a seasoned veteran or otherwise experienced bowler may adjust the weight imbalance of a bowling ball to suit a particular need or for experimental purposes, for example, to increase performance and scores.

Five Examples, including preferred embodiments of a method and apparatus, have been described in detail, an embodiment of an operating system has also been described however it will be understood that many variations are possible. For example, the operating system may be in a different program language other than the version of BASIC used in the described embodiment or the hardware chosen may be other than the SHARP brand pocket computer disclosed and described. The apparatus shown and described may be modified, for example, it will be understood that reference marks may be applied in any of a number of units and the units used in the operating system modified to correspond to the apparatus. It will be further understood that a pocket computer is not necessary to make the necessary determinations.

From the foregoing examples, descriptions and drawings it will be understood that the present invention provides a method and apparatus for locating a hole on a bowling ball and determining the depth of the hole such that a desired, preferred or bowler specified weight change, that is, relative weight, can be established between a pair or pairs of hemispheres as previously described and defined. It will be further understood that a plurality of grip holes or a balance hole may be located and the depth of the hole or holes determined such that, first, the location of the balance hole makes it possible to drill a single hole of determined depth and diameter to create a desired, preferred or bowler specified weight imbalance or dynamic balance in the bowling ball, and second, if desired, locating middle finger, ring finger and thumb grip holes to provide the desired, preferred or bowler specified weight change or imbalance such that the thumb grip hole accounts for one-half (½) of the weight change or imbalance and each finger grip hole accounts for one-quarter (¼) of the weight change or imbalance and that the thumb grip hole is located on a great circle and the finger grip holes are equidistant from the great circle.

It will be understood from the foregoing that an undrilled bowling ball may also refer to a previously drilled bowling ball in which the holes have been plugged. It will be further understood that a reference to a dynamically balanced bowling ball may also refer to a bowling ball in which weight differences have been concentrated as axis weight along an axis of roll.

It will be understood that the preferred embodiments of the bowling ball weight locating method and apparatus have been described and illustrated herein and that the invention is not restricted to the illustrated apparatus and details or operating system.

Other modifications may be made to the embodiments illustrated and described without departing from the spirit of the invention. For example, variations to the wings, base, bowling ball support, arc template, circle template, reference marks, computer or operating system may be provided without departing from the spirit and scope of the invention. It is not intended that the scope of this invention be limited to a particular embodiment. Rather, the scope of the invention is to be determined by the following claims and their equivalents.

What I claim is:

1. A method for locating a manufacturer's reference point on a previously undrilled bowling ball comprising the steps of:
   (a) placing a bowling ball with an internal weight, an outer surface and a diameter in a ball cradle,
   (b) marking a first arc on the surface of the bowling ball in cooperation with the ball cradle, the first arc defining a first side of the bowling ball and a second side of the bowling ball,
   (c) marking a second arc on the surface of the bowling ball in cooperation with the cradle, the second arc perpendicular to the first arc, the second arc defining a finger side of the bowling ball and a thumb side of the bowling ball, the intersection of the first arc and second arc defining a first intersection point as a first reference point,
   (d) marking a great circle on the surface of the bowling ball in cooperation with the cradle, the great circle perpendicular to both the first and the second arc, the great circle defining a top half of the bowling ball and a bottom half of the bowling ball,
   (e) weighing the bowling ball in a dodo scale, and determining:
      1. a relative side weight, the relative side weight corresponding to a difference between a first side weight of the bowling ball and a second side weight of the bowling ball as measured by the dodo scale,
      2. a relative finger weight, the relative finger weight corresponding to a difference between a finger side weight of the bowling ball and a thumb side weight of the bowling ball as measured by the dodo scale,
      3. a relative top weight, the relative top weight corresponding to a difference between a top half weight of the bowling ball and a bottom half weight of the bowling ball as measured by the dodo scale,
   (f) determining a first coordinate and a second coordinate relative to a point defined by the first intersection point and a relationship between the relative side weight, the relative finger weight, the relative top weight, the ball weight and ball diameter,
   (g) marking a second intersection point on the bowling ball surface, the second intersection point determined by the first coordinate and the second coordinate and the second intersection point determines a manufacturer's reference point.

2. The method of claim 1 wherein computing the first coordinate and the second coordinate further comprises the steps of:
   (h) calculating an imbalance vector, as a function of the relative side weight, the relative finger weight and the relative top weight,
   (i) resolving the calculated imbalance vector into a first component and a second component,
   (j) relating the resolved first component and second component to the first coordinate and the second coordinate whereby the second intersection point and the manufacturer's reference point can be located.

3. The method of claim 1 further comprising the steps of:
   (h) determining the magnitude of an imbalance vector, the imbalance vector representing the ball imbalance as the ball was initially placed in the ball cradle,
   (i) determining the magnitude of each of a plurality of component vectors of the imbalance vector,
   (j) determining the length along the second arc on the surface of the ball corresponding to the first coordinate, the length along the second arc relative to the combined magnitude of each of the component vectors,
   (k) determining the length of a third arc on the surface of the ball corresponding to the second coordinate, the length of the third arc relative to the combined magnitude of each of the component vectors.

4. A method for locating a center-of-palm for a bowling ball in accordance with a bowler's balance specifications comprising the steps of:
   (a) placing a bowling ball with an internal weight, an outer surface and a diameter in a ball cradle,
   (b) marking a first arc on the surface of the bowling ball in cooperation with the ball cradle, the first arc defining a first side of the bowling ball and a second side of the bowling ball,
   (c) marking a second arc on the surface of the bowling ball in cooperation with the cradle, the second arc perpendicular to the first arc, the second arc defining a finger side of the bowling ball and a thumb side of the bowling ball, the intersection of the first arc and second arc defining a first intersection point as a first reference point, (d) marking a great circle on the surface of the bowling ball in cooperation with the cradle, the great circle perpendicular to both the first and the second arc, the great circle defining a top half of the bowling ball and a bottom half of the bowling ball,
(e) weighing the bowling ball in a dodo scale, and determining:
  1. a relative side weight, the relative side weight corresponding to a difference between a first side weight of the bowling ball and a second side weight of the bowling ball as measured by the dodo scale,
  2. a relative weight, the relative finger weight corresponding to a difference between a finger side weight of the bowling ball and a thumb side weight of the bowling ball as measured by the dodo scale,
  3. a relative top weight, the relative top weight corresponding to a difference between a top half weight of the bowling ball and a bottom half weight of the bowling ball as measured by the dodo scale,
(f) determining a first coordinate and a second coordinate relative to a point defined by the first intersection point and a relationship between the relative side weight, the relative finger weight, the relative top weight, a desired relative side weight, a desired relative finger weight, a desired relative top weight, a middle finger size, a ring finger size, a thumb size, a hand span, the ball weight and ball diameter,
(g) marking a second intersection point on the bowling ball surface, the second intersection point determined by the first coordinate and the second coordinate and the second intersection point determine a center-of-palm.

5. The method as set forth in claim 4 further comprising the steps of:
(h) determining a depth for the middle finger hole of the grip,
(i) determining a depth for the ring finger of the grip, and
(j) determining a depth for the thumb hole of the grip.

6. A method for dynamically balancing a bowling ball comprising the steps of:
(a) placing an undrilled bowling ball with an internal weight, an outer surface and a diameter in a ball cradle,
(b) marking a first arc on the surface of the undrilled bowling ball in cooperation with the ball cradle, the first arc defining a first side of the bowling ball and a second side of the bowling ball,
(c) marking a second arc on the surface of the undrilled bowling ball in cooperation with the ball cradle, the second arc perpendicular to the first arc, the second arc defining a finger side of the bowling ball and a thumb side of the bowling ball, the intersection of the first arc and second arc defining a first intersection point as a first reference point,
(d) marking a great circle on the surface of the undrilled bowling ball in cooperation with the ball cradle, the great circle perpendicular to both the first and the second arc, the great circle defining a top half of the bowling ball and a bottom half of the bowling ball,
(e) weighing the undrilled bowling ball in a dodo scale, and determining:
  1. a relative side weight, the relative side weight corresponding to a difference between a first side weight of the bowling ball and a second side weight of the bowling ball as measured by the dodo scale,
  2. a relative finger weight, the relative finger weight corresponding to a difference between a finger side weight of the bowling ball and a thumb side weight of the bowling ball as measured by the dodo scale,
  3. a relative top weight, the relative top weight corresponding to a difference between a top half weight of the bowling ball and a bottom half weight of the bowling ball as measured by the dodo scale,
(f) removing the undrilled bowling ball from the ball cradle,
(g) placing a previously drilled bowling ball having a ball track on its surface and a first finger grip hole, a second finger grip hole and a thumb grip hole in the ball cradle,
(h) rotating the previously drilled bowling ball in the ball cradle so that the ball track lies in the bottom hemisphere of the bowling ball as it rests in the ball cradle and adjacent corresponding planar reference marks on the ball cradle,
(i) marking a third arc on the surface of the previously drilled bowling ball in cooperation with the ball cradle,
(j) marking a fourth arc on the surface of the previously drilled bowling ball in cooperation with ball cradle, the intersection of the third and fourth arcs defining an intersection point which identifies an intersection of the surface of the bowling ball and an imaginary line corresponding to an axis of roll,
(k) marking a fifth arc on the surface of the previously drilled bowling ball in cooperation with the ball cradle, located equidistant between the thumb grip hole and first and second finger grip holes,
(l) marking a sixth arc on the surface of the previously drilled bowling ball in cooperation with the ball cradle, the sixth arc passing halfway between the first and second finger grip holes and splitting the thumb grip hole in half, the intersection of the fifth and sixth arcs defining a center of plam,
(m) marking a seventh arc on the surface of the previously drilled bowling ball in cooperation with the ball cradle, the seventh arc being perpendicular to the fifth arc and passing through the axis of roll intersection point and defining another intersection point where the seventh arc and fifth arc intersect,
(n) measuring a first distance along the surface of the previously drilled bowling ball between the center of plam and the other intersection point,
(o) measuring a second distance along the surface of the previously drilled bowling ball between the other intersection point and the axis of roll intersection point,
(p) determining a required weight difference for dynamic balance of the undrilled bowling ball using the first distance, the second distance, the relative side weight, the relative finger weight, and the relative top weight,
(q) determining a location and a diameter and a depth of a single balance hole that could be used to dynamically balance the undrilled bowling ball.

7. The method of claim 6 further comprising the steps of:

(r) determining the desired weight difference for the undrilled bowling ball so as to obtain dynamic balance as a function of a plurality of vectors corresponding to the relative side weight, the relative finger weight, the relative top weight, a desired relative side weight, a desired relative finger weight and a desired relative top weight.

8. The method of claim 6 further comprising the steps of:
(r) proportioning a desired relative side weight, a desired relative finger weight and a desired relative top weight resulting in the determination of the single balance hole, such that, the proportioned weight that results in a dynamically balanced undrilled bowling ball further determines a third finger grip hole, a fourth finger grip hole and a second thumb grip hole in the undrilled bowling ball, whereby, the third finger grip hole and the fourth finger grip hole each create an effective weight difference with respect to dynamic balance of the bowling ball corresponding to one-fourth of a weight difference effectively created by the single balance hole, and the second thumb grip hole creates an effective weight difference also with respect to dynamic balance of the bowling ball corresponding to one-half of the weight difference effectively created by the single balance hole.

9. The method of claim 8 further comprising the steps of:
(s) determining the effect on dynamic balance of the undrilled bowling ball corresponding to a span of a bowler's hand.

10. The method of claim 8 further comprising the steps of:
(s) determining the depths of the third finger grip hole, the fourth finger grip hole and the second thumb grip hole corresponding to the desired relative side weight, the desired relative finger weight and the desired relative top weight such that the undrilled bowling ball is dynamically balanced.

11. The method of claim 10 further comprising the steps of:
(t) determining the desired relative side weight, the desired relative finger side weight and the desired relative top weight when at least one grip insert is inserted in at least one finger or thump grip hole.

12. A method for locating a balance hole for a drilled bowling ball comprising the steps of:
(a) placing a bowling ball with an internal weight, an outer surface a middle finger grip hole, a ring finger grip hole, a thumb grip hole and a diameter in a ball cradle,
(b) marking a first arc on the surface of the bowling ball in cooperation with the ball cradle, the first arc defining a first side of the bowling ball and a second side of the bowling ball,
(c) marking a second arc on the surface of the bowling ball in cooperation with the cradle, the second arc perpendicular to the first arc, the second arc defining a finger side of the bowling ball and a thumb side of the bowling ball, the intersection of the first arc and second arc devining a first intersection point as a reference point,
(d) marking a great circle on the surface of the bowling ball in cooperation with the cradle, the great circle perpendicular to both the first and the second arc, the great circle defining a top half of the bowling ball and a bottom half of the bowling ball,
(e) weighing the bowling ball in a dodo scale, and determining:
 1. a relative side weight, the relative side weight corresponding to a difference between a first side weight of the bowling ball and a second side weight of the bowling ball as measured by the dodo scale,
 2. a relative finger weight, the relative finger weight corresponding to a difference between a finger side weight of the bowling ball and a thumb side weight of the bowling ball as measured by the dodo scale,
 3. a relative top weight, the relative top weight corresponding to a difference between a top half weight of the bowling ball and a bottom half weight of the bowling ball as measured by the dodo scale,
(f) determining a first coordinate and a second coordinate relative to a point defined by the first intersection point and a relationship between the relative side weight, the relative finger weight, the relative top weight, a desired relative side weight, a desired relative finger weight, a desired relative top weight the ball weight and ball diameter,
(g) marking another intersection point on the bowling ball surface, the second intersection point determined by the first coordinate and the second coordinate whereby the second intersection point corresponds to a location for a balance hole.

13. A method for dynamically balancing a previously drilled bowling ball comprising the steps of:
(a) placing a bowling ball with an internal weight, an outer surface, a middle finger grip hole, a ring finger grip hole, a thumb grip hole and a diameter in a ball cradle,
(b) marking a first arc on the surface of the bowling ball in cooperation with the ball cradle, the first arc defining a first side of the bowling ball and a second side of the bowling ball,
(c) marking a second arc on the surface of the bowling ball in cooperation with the cradle, the second arc perpendicular to the first arc, the second arc defining a finger side of the bowling ball and a thumb side of the bowling ball, the intersection of the first arc and second arc defining a first intersection point as a first reference point,
(d) marking a great circle on the surface of the bowling ball in cooperation with the cradle, the great circle perpendicular to both the first and the second arc, the great circle defining a top half of the bowling ball and a bottom half of the bowling ball,
(e) weighing the bowling ball in a dodo scale, and determining:
 1. a relative side weight, the relative side weight corresponding to a difference between a first side weight of the bowling ball and a second side weight of the bowling ball as measured by the dodo scale,
 2. a relative finger weight, the relative finger weight corresponding to a difference between a finger side weight of the bowling ball and a thumb side weight of the bowling ball as measured by the dodo scale,
 3. a relative top weight, the relative top weight corresponding to a difference between a top half weight of the bowling ball and a bottom half weight of the bowling ball as measured by the dodo scale, (f) locating the position of a ball track on the bowling ball, (g) determining a first coordinate and a second coordinate relative to a point defined by the first reference point and an axis of roll and a relationship between the relative side weight, the relative finger weight, the relative top weight, the location of the ball track, the ball weight and ball diameter, (h) locating a second reference point on the bowling ball surface, the second reference point corresponds to a location for a balance hole.

14. A bowling ball weight locating apparatus, comprising:

(a) means for supporting a bowling ball, (b) first means for defining a plane, the first means removably operatively associated with the support means, (c) second means for definint another plane, the other plane perpendicular to the one plane, the second means removably operatively associated with the support means, and (d) means for locating a semicircular arc on a bowling ball's surface, the locating means removably supported by the support means and either the first means or the second means.

15. The bowling ball weight locating apparatus as set forth in claim 14 further comprising:

(e) means for rotatably supporting the bowling ball.

16. The bowling ball weight locating apparatus as set forth in claim 14 further comprising:

(e) at least one of either the first or second plane defining means including an arcuate reference scale.

17. The bowling ball weight locating apparatus as set forth in claim 14 further comprising:

(e) means for locating a great circle on the surface of the bowling ball, the great circle locating means removably supported by the first and second means.

* * * * *